(12) United States Patent
Alden-Danforth et al.

(10) Patent No.: US 8,932,573 B2
(45) Date of Patent: Jan. 13, 2015

(54) MASCARA COMPOSITIONS COMPRISING A SEMICRYSTALLINE POLYMER, A SILICONE ELASTOMER, AND A HYDROPHILIC GELLING AGENT

(71) Applicant: L'Oreal, Paris (FR)

(72) Inventors: Ethan Alden-Danforth, Jersey City, NJ (US); Angeles Fonolla-Moreno, Westfield, NJ (US)

(73) Assignee: L'Oreal, Paris (FR)

( * ) Notice: Subject to any disclaimer, the term of this patent is extended or adjusted under 35 U.S.C. 154(b) by 139 days.

(21) Appl. No.: 13/848,822

(22) Filed: Mar. 22, 2013

(65) Prior Publication Data

US 2014/0286893 A1 Sep. 25, 2014

(51) Int. Cl.
*A61K 8/81* (2006.01)
*A61Q 1/10* (2006.01)
*A61K 8/895* (2006.01)

(52) U.S. Cl.
CPC ............... *A61K 8/8135* (2013.01); *A61Q 1/10* (2013.01); *A61K 8/8152* (2013.01); *A61K 8/895* (2013.01); *A61K 2800/87* (2013.01)
USPC ...................................... 424/78.31

(58) Field of Classification Search
None
See application file for complete search history.

(56) References Cited

U.S. PATENT DOCUMENTS

| | | | |
|---|---|---|---|
| 5,162,410 A | 11/1992 | Sweet | |
| 6,338,839 B1 | 1/2002 | Auguste et al. | |
| 8,211,415 B2 | 7/2012 | Pays et al. | |
| 2003/0165451 A1 | 9/2003 | Lennon et al. | |
| 2006/0078520 A1 | 4/2006 | Pays et al. | |
| 2006/0216257 A1 | 9/2006 | Pays et al. | |
| 2006/0233732 A1 | 10/2006 | Lezer | |
| 2007/0148114 A1 | 6/2007 | Jager Lezer et al. | |
| 2007/0196306 A1 | 8/2007 | Jager Lezer et al. | |
| 2008/0199421 A1* | 8/2008 | Lorant .................. | 424/78.03 |
| 2009/0317350 A1 | 12/2009 | Lu et al. | |
| 2010/0068163 A1 | 3/2010 | Lu | |
| 2010/0092417 A1 | 4/2010 | Narebski et al. | |
| 2010/0215605 A1 | 8/2010 | Arditty et al. | |
| 2010/0242984 A1 | 9/2010 | Arditty et al. | |
| 2010/0303931 A1 | 12/2010 | Feltin et al. | |
| 2010/0319721 A1 | 12/2010 | Pays et al. | |
| 2011/0150805 A1 | 6/2011 | Kergosien et al. | |
| 2011/0155162 A1 | 6/2011 | Arditty et al. | |
| 2011/0165102 A1 | 7/2011 | Arditty et al. | |
| 2011/0236332 A1 | 9/2011 | Dop | |
| 2012/0093560 A1 | 4/2012 | Arditty | |
| 2012/0301414 A1 | 11/2012 | Noel et al. | |

FOREIGN PATENT DOCUMENTS

| | | |
|---|---|---|
| EP | 611170 A1 | 8/1994 |
| EP | 811336 A1 | 12/1997 |
| EP | 811337 A1 | 12/1997 |
| EP | 842620 A1 | 5/1998 |
| FR | 2607373 A1 | 6/1988 |
| FR | 2859100 A1 | 3/2005 |
| FR | 2859101 A1 | 3/2005 |
| FR | 2881642 A1 | 8/2006 |
| FR | 2917610 A1 | 12/2008 |
| FR | 2934494 A1 | 2/2010 |
| FR | 2943913 A1 | 10/2010 |
| FR | 2954146 A1 | 6/2011 |
| WO | 2004073626 A2 | 9/2004 |
| WO | 2006013411 A1 | 2/2006 |
| WO | 2006058793 A1 | 6/2006 |
| WO | 2006058795 A1 | 6/2006 |
| WO | 2007054494 A1 | 5/2007 |
| WO | 2007054830 A2 | 5/2007 |
| WO | 2007066309 A2 | 6/2007 |
| WO | 2008046762 A1 | 4/2008 |
| WO | 2008046763 A1 | 4/2008 |
| WO | 2009053635 A1 | 4/2009 |
| WO | 2009130090 A1 | 10/2009 |
| WO | 2010010511 A2 | 1/2010 |
| WO | 2010057920 A2 | 5/2010 |
| WO | 2012168102 A2 | 12/2012 |
| WO | 2013010590 A1 | 1/2013 |

\* cited by examiner

*Primary Examiner* — Brian Gulledge
(74) *Attorney, Agent, or Firm* — L'Oreal USA

(57) ABSTRACT

Disclosed herein are cosmetic compositions for making up and/or coating keratinous fibers, said composition comprising: (a) at least one semicrystalline polymer; (b) at least one silicone elastomer blend comprising at least one silicone cross-polymer dispersed in at least one oil; (c) at least one hydrophilic gelling agent; and (d) an aqueous phase. Also disclosed herein are methods for making up and/or enhancing the appearance of keratinous fibers comprising applying said compositions to the keratinous fibers.

24 Claims, No Drawings

MASCARA COMPOSITIONS COMPRISING A SEMICRYSTALLINE POLYMER, A SILICONE ELASTOMER, AND A HYDROPHILIC GELLING AGENT

FIELD OF THE DISCLOSURE

The disclosure relates to cosmetic compositions comprising a semicrystalline polymer, a silicone elastomer, a hydrophilic gelling agent, and an aqueous phase. Cosmetic compositions according to various embodiments of the disclosure are stable and when applied onto keratinous fibers, for example, the eyelashes, may provide one or more improved properties such as improved volume and/or thickening, lengthening, improved resistance to clumping and/or caking, and/or improved ease of removal. The disclosure further relates to methods for making up and/or enhancing the appearance of keratinous fibers comprising applying said composition to the keratinous fibers.

BACKGROUND

Cosmetic compositions which enhance the appearance of human keratinous fibers such as eyelashes, eyebrows and hair, including false eyelashes and hair pieces are highly desirable to consumers. In particular, the compositions of the invention may be makeup compositions, makeup bases, compositions for applying on makeup, also known as topcoats, or even cosmetic treatment compositions for treating keratinous fibers. More generally, the invention relates to a mascara.

Mascara compositions are known and used in the cosmetic field to impart thickness, color, and/or length to the eyelashes. There are also two general types of mascaras—the waterproof or water resistant type and the washable type. Thus, several different mascara formulations have been developed in the art using various cosmetic ingredients depending on the desired cosmetic properties. For instance, it is known in the art that the inclusion of certain ingredients in a mascara composition can improve various properties, such as the ability of the composition to thicken the eyelashes. For example, the inclusion of fibers may enhance the lengthening or volumizing properties of a mascara composition.

However, there still exists a need in the cosmetic art for "clean volume" mascara compositions, e.g., compositions that lengthen and separate the lashes and impart a smooth and homogeneous deposit, while also volumizing or thickening the lashes with minimal or no clumping or caking. As such, there is a continuous need to invent novel cosmetic compositions which demonstrate one or more of the above-mentioned improved properties and at the same time, are stable and/or demonstrate desirable textures.

It has now been surprisingly discovered that by incorporating (1) at least one semicrystalline polymer, (2) at least one silicone elastomer blend comprising at least one silicone cross-polymer dispersed in at least one oil; (3) at least hydrophilic gelling agent; and (4) an aqueous phase into a cosmetic composition, a stable composition and desirable cosmetic properties are achieved. When said composition is a mascara composition employed to coat or treat the eyelashes, the cosmetic benefits obtained are improved thickening and/or volume, lengthening, improved lash separation, smooth and homogeneous deposit, ease of application, improved resistance to clumping and/or caking, and/or improved ease of removal. It was also surprisingly discovered that the compositions of the present invention have a novel texture wherein said compositions are smooth and/or creamy and impart a smooth and soft feel to the coated substrate.

SUMMARY OF THE INVENTION

The present invention relates to cosmetic compositions for making up and/or coating keratinous fibers, said composition containing:
(a) at least one semicrystalline polymer,
(b) at least one silicone elastomer blend comprising at least one silicone cross-polymer dispersed in at least one oil;
(c) at least one hydrophilic gelling agent; and
(d) an aqueous phase.

Furthermore, the present invention relates to a method of making up and/or enhancing the appearance of keratinous fibers comprising applying to the keratinous fibers, the above described composition.

In various embodiments of the disclosure, the present invention relates to cosmetic compositions for making up and/or coating the eyelashes and/or eyebrows comprising at least one semicrystalline polymer; at least one silicone elastomer blend comprising at least one silicone cross-polymer dispersed in at least one oil; at least one hydrophilic gelling agent; and an aqueous phase. Preferably, the cosmetic composition is a mascara composition. Preferably, the cosmetic composition is an emulsion, such as for example, an oil in water emulsion.

The present invention also relates to methods of treating, coating, caring for and/or making up eyelashes and/or eyebrows comprising applying the cosmetic compositions of the present invention to eyelashes and/or eyebrows in an amount sufficient to treat, care for and/or make up the eyelashes and/or eyebrows. Preferably, the cosmetic composition is a mascara composition. Preferably, the cosmetic composition is an emulsion, such as for example, an oil in water emulsion.

Moreover, the present invention relates to methods of improving the volumizing and/or thickening, lengthening, lash separating, resistance to clumping and/or caking properties of a cosmetic composition onto eyelashes and/or eyebrows, comprising adding to said composition comprising at least one semicrystalline polymer; at least one silicone elastomer blend comprising at least one silicone cross-polymer dispersed in at least one oil; at least one hydrophilic gelling agent; and an aqueous phase. Preferably, the cosmetic composition is a mascara composition. Preferably, the cosmetic composition is an emulsion, such as for example, an oil in water emulsion.

In other embodiments, the present invention relates to methods of improving the homogeneity of deposition and ease of application of a make up composition onto keratinous fibers by providing a cosmetic composition of the present invention. Preferably, the cosmetic composition is a mascara composition. Preferably, the cosmetic composition is an emulsion, such as for example, an oil in water emulsion.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

The term "keratinous fibers" means the eyelashes, the eyebrows, bodily hair or head hair.

The term "mascara" means a composition intended to be applied to keratinous fibers, especially to the eyelashes: it may be an eyelash makeup composition, an eyelash makeup base (also known as a base coat), a composition to be applied onto a mascara (also known as a top coat), or a cosmetic eyelash treatment composition. The mascara is more particularly intended for human eyelashes, but also false eyelashes.

The most conventional mascaras usually have a pasty texture and are conditioned in a container comprising a reservoir equipped with a drainer wiper? and an applicator, especially in the form of a brush or a comb, and which are applied by taking up product in the reservoir using the applicator, passing the applicator through the drainer wiper in order to remove the excess product, and then placing the applicator impregnated with mascara in contact with the eyelashes.

"Film former" or "film forming polymer" as used herein means a polymer or resin that leaves a film on the substrate to which it is applied, for example, after a solvent accompanying the film forming polymer has evaporated, absorbed into and/or dissipated on the substrate.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100 degrees C.

"Non-volatile", as used herein, means having a flash point of greater than about 100 degree C.

The compositions and methods of the present invention can comprise, consist of, or consist essentially of the essential elements and limitations of the invention described herein, as well as any additional or optional ingredients, components, or limitations described herein or otherwise useful.

It was unexpectedly and surprisingly discovered that the cosmetic composition of the present invention, when applied as a mascara composition onto keratinous fibers such as eyelashes, formed a film or coating on said fibers that provided greater volume, as well as a smooth and soft feel to the coated fibers.

It was unexpectedly and surprisingly discovered that the combination of at least one semicrystalline polymer; at least one silicone elastomer blend comprising at least one silicone cross-polymer dispersed in at least one oil; at least one hydrophilic gelling agent; and an aqueous phase produced a composition which, when applied onto keratinous fibers, had improved thickening or volumizing properties and did not clump nor cake on the keratinous fibers. It was also surprisingly found that the compositions of the present invention were easy to apply, deposited a homogenous coating, imparted a smooth and soft feel to keratinous fibers such as the eyelashes and were easily washable.

Semicrystalline Polymer

The cosmetic composition of the invention includes at least one semicrystalline polymer.

The term "semicrystalline polymer" is used to mean polymers having a crystallizable portion, a crystallizable pendant chain, or a crystallizable sequence in its backbone, and an amorphous portion in the backbone, and that also presents a first-order reversible change-of-phase temperature, in particular for melting (solid-liquid transition). When the crystallizable portion is in the form of a crystallizable sequence of the polymer backbone, the amorphous portion of the polymer is in the form of an amorphous sequence. The semicrystalline polymer is then a sequenced copolymer, e.g. of the diblock, triblock, or multiblock type, having at least one crystallizable sequence and at least one amorphous sequence. The term "sequence" generally means at least five identical repetition motifs. The crystallizable sequence(s) is/are then of a chemical nature that is different from the amorphous sequence(s).

The semicrystalline polymer has a melting temperature greater than or equal to 30 degrees centigrade, in particular lying in the range 30 degrees centigrade to 80 degrees centigrade, preferably in the range 30 degrees centigrade to 60 degrees centigrade. The melting temperature is a first-order change-of-state temperature.

This melting temperature may be measured by any known method, and in particular by using differential scanning calorimetry (DSC).

Advantageously, the semicrystalline polymer(s) to which an embodiment applies presents a number average molecular mass that is greater than or equal to 1000. Advantageously, the semicrystalline polymer(s) of the composition have a number average molecular mass Mn lying in the range 2000 to 800,000, preferably in the range 3000 to 500,000, better in the range 4000 to 150,000, and in particular less than 100,000, better in the range 4000 too 99,000. Preferably, they present a number average molecular mass greater than 5600, i.e. lying in the range 5700 to 99,000. The term "crystallizable chain or sequence" is used to mean a chain or sequence that, on its own, would pass from the amorphous state to the crystalline state in reversible manner depending on whether the temperature is above or below the melting temperature. A "chain" in the meaning of an embodiment is a group of atoms that is pendant or lateral relative to the backbone of the polymer. A sequence is a group of atoms forming part of the backbone, which group constitutes one of the repetitive motifs of the polymer. Advantageously, the "crystallizable pendant chain" may be a chain having at least 6 carbon atoms.

The semicrystalline polymer may be selected from sequenced copolymers including at least one crystallizable sequence and at least one amorphous sequence, homopolymers, and copolymers having at least one crystallizable lateral or side chain per repetition motif, and mixtures thereof.

By way of example, such polymers are described in document EP 1 396 259.

Semi-crystalline polymers containing crystallizable side chains may be homopolymers or copolymers comprising from 50% to 100% by weight of units resulting from the polymerization of one or more monomers bearing a crystallizable hydrophobic side chain.

Polymers bearing in the skeleton at least one crystallizable block are especially block copolymers consisting of at least two blocks of different chemical nature, one of which is crystallizable. Examples are block copolymers of olefin or of cycloolefin containing a crystallizable chain, and copolymers containing at least one crystallizable block, the rest of the copolymer being amorphous (at room temperature). These copolymers may also contain two crystallizable blocks of different chemical nature.

In particular exemplary embodiments, the polymer comes from a crystallizable chain monomer selected from C14 to C30 saturated alkyl(meth)acrylates.

As a particular example of a structuring semicrystalline polymer usable in the composition, mention may be made of Intelimer® products from the company Landec.

These polymers are in a form that is solid at ambient temperature (25 degrees centigrade). They carry crystallizable side chains.

According to the present invention, a preferred semicrystalline polymer is poly C10-30 alkyl acrylate, also known under the tradename, Intelimer® IPA 13-1 NG and commercially available from the company, Air Products and Chemicals.

The at least one semicrystalline polymer(s) may be employed in the cosmetic composition of the present invention in an amount ranging from about 0.1 to about 20% by weight, or from about 0.5 to about 10% by weight, or from about 1 to about 5% by weight, relative to the total weight of the composition, including all ranges and subranges therebetween.

In other embodiments, the at least one semicrystalline polymer(s) may be employed in the cosmetic composition of the present invention in an amount of about 2% by weight, or about 2.5% by weight, or about 3% by weight, relative to the total weight of the composition.

The at least one semicrystalline polymer of the present invention is preferably soluble in a non-polar solvent such as non-polar oils or in a liquid fatty phase.

Silicone Elastomer Blends

As described herein, the cosmetic compositions comprise at least one silicone elastomer blend. Silicone elastomer blends useful according to various embodiments of the disclosure may comprise at least one silicone cross-polymer dispersed in at least one oil.

The at least one silicone cross-polymer may, in certain embodiments, be chosen from dimethicone/vinyl dimethicone cross-polymers and dimethicone/phenyl vinyl dimethicone cross-polymers. In other embodiments, the silicone cross-polymer may be modified by one or more groups chosen from alkyl, polyether, polyglycerin groups. For instance, the alkyl modified silicone cross-polymers may be chosen from vinyl dimethicone/lauryl dimethicone cross-polymers, cetearyl dimethicone cross-polymers, and $C_{30}$-$C_{45}$ alkyl cetearyl dimethicone cross-polymers. Non-limiting examples of polyether modified silicone cross-polymers include dimethicone/PEG-10/15 cross-polymers. Suitable alkyl and polyether modified silicone cross-polymers may be chosen, for example, from PEG-10/lauryl dimethicone cross-polymers and PEG-15/lauryl dimethicone cross-polymers. Exemplary polyglycerin modified silicone cross-polymers include dimethicone/polyglycerin-3 cross-polymers and lauryl dimethicone/polyglycerin-3 cross-polymers.

The silicone cross-polymer may be dispersed in at least one oil. In certain embodiments, the oil may be chosen from silicone oils, such as cyclic and linear organopolysiloxanes. Cyclic organopolysiloxanes may include, for example, cyclotetrasiloxane; cyclopentasiloxane; and methylated cyclic organopolysiloxanes, e.g., octamethylcyclotetrasiloxane and decamethylcyclopentasiloxane. Non-limiting examples of linear organopolysiloxanes include low molecular weight dimethicones; high molecular weight dimethicones; alkyl derivatives of linear organopolysiloxanes, e.g., cetyl dimethicone and lauryl trimethicone; aryl derivatives of linear organopolysiloxanes, e.g., phenyl trimethicone; and hydroxylated derivatives of linear organopolysiloxanes, e.g., dimethiconol. In other embodiments, the oil may be chosen from organic oils, such as mineral oil; linear and branched alkanes, e.g., isododecane; triethylhexanoin; and squalane.

The at least one silicone cross-polymer may, in one embodiment, comprise from about 5% to about 35% by weight, relative to the total weight of the silicone elastomer blend, for example, from about 10% to about 20% by weight, or from about 25% to about 35% by weight, or from about 20% to about 30% by weight, including all ranges and subranges therebetween. The at least one oil may comprise from about 65% to about 95% by weight, relative to the total weight of the silicone elastomer blend, such as from about 80% to about 90% by weight, or from about 65% to about 75% by weight, or from about 70% to about 80% by weight, including all ranges and subranges therebetween.

According to one embodiment, the silicone elastomer blend comprises from about 20% to about 30% of dimethicone/vinyl dimethicone cross-polymer. In another embodiment, the silicone elastomer blend comprises from about 70% to about 80% by weight of dimethicone. According to a further embodiment, the silicone elastomer blend comprises from about 20% to about 30% of dimethicone/vinyl dimethicone cross-polymer and from about 70% to about 80% by weight dimethicone.

Non-limiting examples of commercially available silicone elastomer blends include the products sold under the KSG product line by Shin-Etsu, such as KSG-15, KSG-16, KSG-210, and KSG-18, and the products sold under the VELVESIL product line by Momentive, such as VELVESIL 125 and VELVESIL DM.

The at least one silicone elastomer blend may be present in the cosmetic composition in an amount ranging from about 0.1% to about 40% by weight, such as from about 0.5% to about 20% by weight, or from about 1% to about 10% by weight, or from about 2% to about 8% by weight, or from about 2% to about 6% by weight, relative to the total weight of the cosmetic composition, including all ranges and subranges therebetween. In other embodiments, the at least one silicone elastomer blend may be present in an amount greater than about 2% by weight, or it may be present in an amount of about 3% by weight, or about 4% by weight, or about 5% by weight, or about 6% by weight, relative to the total weight of the cosmetic composition.

Hydrophilic Gelling Agents

The cosmetic compositions of the present invention include at least one hydrophilic gelling agent. This gelling agent may more particularly be chosen from acrylic polymers described as follows:

a—Hydrophilic Acrylic Polymers

According to the invention, the term "hydrophilic acrylic polymers" especially means non-hydrophobic and non-amphiphilic acrylic polymers.

Said hydrophilic acrylic polymers according to the invention are either polyacrylamidomethylpropanesulfonic acid (AMPS®) acrylic polymers or acrylic acid polymers.

The presence of this hydrophilic acrylic polymer makes it possible especially to obtain a composition that has good stability properties.

Among the hydrophilic acrylic polymers that may be mentioned are the following polymers:

Acrylic Polymers Comprising at Least One Monomer Bearing a Sulfonic Group

According to a first embodiment, the hydrophilic acrylic polymer used according to the invention comprises at least one monomer bearing a sulfonic group.

The polymers used in accordance with the invention are homopolymers that may be obtained from at least one ethylenically unsaturated monomer bearing a sulfonic group, which may be in free form or partially or totally neutralized form.

Preferentially, the polymers in accordance with the invention are partially or totally neutralized with a mineral base (sodium hydroxide, potassium hydroxide or aqueous ammonia) or an organic base such as monoethanolamine, diethanolamine, triethanolamine, an aminomethylpropanediol, N-methylglucamine, basic amino acids, for instance arginine and lysine, and mixtures of these compounds. They are generally neutralized.

In the present invention, the term "neutralized" means polymers that are totally or virtually totally neutralized, i.e. at least 90% neutralized.

The polymers used in the composition of the invention generally have a number-average molecular weight ranging from 1000 to 20 000 000 g/mol, preferably ranging from 20 000 to 5 000 000 g/mol and even more preferentially from 100 000 to 1 500 000 g/mol.

These polymers according to the invention may be crosslinked or noncrosslinked.

The monomers bearing a sulfonic group of the polymer used in the composition of the invention are especially chosen from vinylsulfonic acid, styrenesulfonic acid, (meth)acrylamido($C_1$-$C_{22}$)alkylsulfonic acids, N—($C_1$-$C_{22}$)alkyl(meth)acrylamido($C_1$-$C_{22}$)alkylsulfonic acids such as undecylacrylamidomethanesulfonic acid, and also partially or totally neutralized forms thereof, and mixtures thereof.

According to one preferred embodiment of the invention, the monomers bearing a sulfonic group are chosen from (meth)acrylamido($C_1$-$C_{22}$)alkylsulfonic acids, for instance acrylamidomethanesulfonic acid, acrylamidoethanesulfonic acid, acrylamidopropanesulfonic acid, 2-acrylamido-2-methylpropanesulfonic acid, 2-methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid and 2-acrylamido-2,6-dimethyl-3-heptanesulfonic acid, and also partially or totally neutralized forms thereof, and mixtures thereof.

More particularly, 2-acrylamido-2-methylpropanesulfonic acid (AMPS®), and also partially or totally neutralized forms thereof, is used.

When the polymers are crosslinked, the crosslinking agents may be chosen from the polyolefinically unsaturated compounds commonly used for crosslinking polymers obtained by free-radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl(meth)acrylate, allylic ethers of alcohols of the sugar series, or other allylic or vinyl ethers of polyfunctional alcohols, and also the allylic esters of phosphoric and/or vinylphosphonic acid derivatives, or mixtures of these compounds.

According to one preferred embodiment of the invention, the crosslinking agent is chosen from methylenebisacrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The homopolymer of monomers bearing a sulfonic group may be crosslinked with one or more crosslinking agents.

These homopolymers are generally crosslinked and neutralized, and they may be obtained according to the preparation process comprising the following steps:

(a) the monomer such as 2-acrylamido-2-methylpropanesulfonic acid in free form is dispersed or dissolved in a solution of tert-butanol or of water and tert-butanol;

(b) the monomer solution or dispersion obtained in (a) is neutralized with one or more mineral or organic bases, preferably aqueous ammonia $NH_3$, in the amount making it possible to obtain a degree of neutralization of the sulfonic acid functions of the polymer ranging from 90% to 100%;

(c) the crosslinking monomer(s) are added to the solution or dispersion obtained in (b);

(d) a standard free-radical polymerization is performed in the presence of free-radical initiators at a temperature ranging from 10 to 150° C.; the polymer precipitates in the tert-butanol-based solution or dispersion.

The preferred AMPS® homopolymers are generally characterized in that they comprise, randomly distributed:

a) from 90% to 99.9% by weight of units of general formula (II) below:

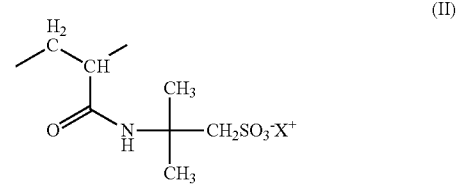

(II)

in which $X^+$ denotes a proton, an alkali metal cation, an alkaline-earth metal cation or the ammonium ion, not more than 10 mol % of the cations $X^+$ possibly being protons $H^+$;

b) from 0.01% to 10% by weight of crosslinking units derived from at least one monomer containing at least two olefinic double bonds; the weight proportions being defined relative to the total weight of the polymer.

The homopolymers according to the invention that are more particularly preferred comprise from 98% to 99.5% by weight of units of formula (II) and from 0.2% to 2% by weight of crosslinking units.

A polymer of this type that may especially be mentioned is the crosslinked and neutralized 2-acrylamido-2-methylpropanesulfonic acid homopolymer sold by the company Clariant under the trade name Hostacerin® AMPS (CTFA name: ammonium polyacryldimethyltauramide).

Acrylamide/AMPS® Copolymers

According to another embodiment, the hydrophilic acrylic polymer is a crosslinked anionic copolymer formed from units derived from the reaction between (i) acrylamide (monomer 1), (ii) 2-acrylamido-2-methylpropanesulfonic acid (monomer 2, referred to hereinbelow for convenience as AMPS®) and (iii) at least one polyolefinically unsaturated compound (monomer 3), constituting here the crosslinking agent.

The crosslinked anionic copolymers used in the context of the present invention are products that are already known per se and their preparation has been described especially in patent application EP-A-0 503 853, the content of which is consequently included in its entirety by reference in the present description.

The above copolymers may thus be obtained conventionally according to the emulsion polymerization technique from three different comonomers included in their constitution.

The polyolefinically unsaturated monomers used as crosslinking agents for the preparation of the copolymers in accordance with the invention are preferably chosen from the group formed by methylenebisacrylamide, allyl sucrose and pentaerythritol. Even more preferentially, use is made of methylenebisacrylamide.

Preferably, said polyolefinically unsaturated compound is present in the copolymer in a concentration of between 0.06 and 1 mmol per mole of the monomer units as a whole.

The ratio, expressed in mol %, between acrylamide and AMPS® is preferentially between 85/15 and 15/85, advantageously between 70/30 and 30/70, even more preferentially between 65/35 and 35/65 and even more particularly between 60/40 and 40/60. In addition, AMPS is generally at least partially neutralized in the form of a salt, for example with sodium hydroxide, with potassium hydroxide or with a low molecular weight amine such as triethanolamine, or mixtures thereof.

A crosslinked copolymer that is particularly preferred in the context of the implementation of the present invention corresponds to the one prepared in Example 1 of patent application EP-A-0 503 853 mentioned above, and which is then in the form of a water-in-oil inverse emulsion. More precisely, this copolymer is formed from 60 mol % of acrylamide and 40 mol % of the sodium salt of AMPS®, and it is crosslinked with methylenebisacrylamide in a proportion of 0.22 mmol per mole of the total monomer mixture. The final water-in-oil inverse emulsion preferably contains about 40% by weight of crosslinked copolymer as defined above and about 4% by weight of an ethoxylated fatty alcohol with an HLB of about 12.5.

Crosslinked copolymers that are more particularly used according to the invention are the products sold under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) sold by the company SEPPIC, or Simulgel EG (CTFA name: sodium acrylate/sodium acryloyldimethyltaurate copolymer/isohexadecane/polysorbate 80).

Other Hydrophilic Acrylic Polymers

As other hydrophilic acrylic polymers that may be used according to the invention, mention may also be made of:

homopolymers or copolymers of acrylic or methacrylic acids or salts thereof and esters thereof, such as the products sold under the names Carbopol 934, 940, 954, 981 and 980 by the company Noveon, Synthalen L® from the company 3V, sodium polymethacrylate sold under the name Darvan No. 7® by the company Vanderbilt, the products sold under the names Versicol F or Versicol K by the company Allied Colloid, Ultrahold 8 by the company Ciba Geigy and polyacrylic acids of Synthalen K type, polyacrylates and polymethacrylates such as glyceryl acrylate polymers, and in particular copolymers of glyceryl acrylate and of acrylic acid, such as the products sold under the names Lubrajel® MS, Lubrajel® CG, Lubrajel® DV, Lubrajel® NP, Lubrajel® Oil, Lubrajel® Oil BG, Lubrajel® PF, Lubrajel® TW and Lubrajel® WA by the company Guardian Laboratories. Use is preferably made of Lubrajel® MS, polyacrylic acid/alkyl acrylate copolymers of Pemulen type, copolymers of acrylic acid salt/vinyl alcohol, such as the product sold under the name Hydragen FN® from Cognis, and mixtures thereof.

b—Amphiphilic Acrylic Polymers

Such polymers may be derived from the AMPS® products described previously. These polymers comprise both a hydrophilic part and a hydrophobic part comprising at least one fatty chain. They are therefore amphiphilic polymers.

A fatty chain of such a polymer may comprise from 7 to 30 carbon atoms and in particular from 8 to 22 carbon atoms.

A hydrophobic AMPS® copolymer in accordance with the invention may have a weight-average molecular weight ranging from 50 000 to 10 000 000, in particular from 100 000 to 8 000 000 and more particularly from 100 000 to 7 000 000.

A hydrophobic AMPS® copolymer according to the invention may be crosslinked or noncrosslinked.

Among the crosslinking agents that may be suitable for use, mention may be made, in a nonlimiting manner, of methylenebisacrylamide, allyl methacrylate and trimethylolpropane triacrylate (TMPTA).

The degree of crosslinking may range from 0.01 mol % to 10 mol % and particularly from 0.2 mol % to 2 mol % relative to the polymer.

An amphiphilic AMPS® polymer that is suitable for use in the invention may be chosen, for example, from statistical amphiphilic AMPS polymers modified by reaction with a $C_6$-$C_{22}$ n-monoalkylamine or di-n-alkylamine such as those described in patent application WO 00/31154.

These polymers may also contain other ethylenically unsaturated hydrophilic monomers chosen, for example, from acrylic acid, methacrylic acid or alkyl-substituted derivatives thereof or esters thereof obtained with mono- or polyalkylene glycols, acrylamide, methacrylamide, vinylpyrrolidone, itaconic acid and maleic acid, or mixtures thereof.

A polymer of the invention may be chosen from amphiphilic polymers of AMPS® and of at least one ethylenically unsaturated monomer comprising at least one hydrophobic part containing from 7 to 30 carbon atoms, in particular from 8 to 22 carbon atoms and more particularly from 12 to 20 carbon atoms.

The hydrophobic part may be a saturated or unsaturated linear (for example n-octyl, n-decyl, n-hexadecyl, n-dodecyl or oleyl), branched (for example isostearic) or cyclic (for example cyclododecane or adamantane) alkyl radical.

An ethylenically unsaturated hydrophobic monomer that is suitable for use in the invention may be chosen from the acrylates or acrylamides of formula (1) below:

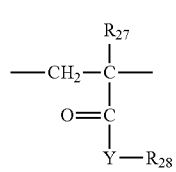

(1)

in which:
$R_{27}$ denotes a hydrogen atom or a linear or branched $C_1$-$C_6$ alkyl radical (preferably methyl),
Y denotes O or NH;
$R_{28}$ denotes a hydrophobic radical comprising a fatty chain containing from 7 to 30 carbon atoms, preferably from 8 to 22 and more particularly from 12 to 20 carbon atoms.

The hydrophobic radical $R_{28}$ is chosen from saturated or unsaturated linear $C_7$-$C_{22}$ alkyl radicals (for example n-octyl, n-decyl, n-hexadecyl, n-dodecyl or oleyl), branched alkyl radicals (for example isostearic) or cyclic alkyl radicals (for example cyclododecane or adamantane); $C_7$-$C_{18}$ alkylperfluoro radicals (for example the group of formula $(CH_2)_2(CF_2)_9$—$CF_3$); the cholesteryl radical or a cholesterol ester, for instance cholesteryl hexanoate; aromatic polycyclic groups, for instance naphthalene or pyrene.

Among these radicals, linear and branched alkyl radicals are more particularly preferred.

According to one embodiment of the invention, the hydrophobic radical $R_{28}$ may also comprise at least one alkylene oxide unit and in particular a polyoxyalkylene chain.

A polyoxyalkylene chain may be formed from ethylene oxide units and/or propylene oxide units and even more particularly be formed solely from ethylene oxide units.

The number of moles of oxyalkylene units may generally range from 1 to 30 mol, more particularly from 2 to 25 mol and even more particularly from 3 to 20 mol.

Among the AMPS® amphiphilic polymers that are suitable for use in the invention, mention may be made of:
crosslinked or noncrosslinked, neutralized or non-neutralized copolymers comprising from 15% to 60% by weight of AMPS units and from 40% to 85% by weight of ($C_8$-$C_{16}$) alkyl(meth)acrylamide units or of ($C_8$-$C_{16}$)alkyl(meth)acrylate units relative to the polymer, such as those described in patent application EP-A-0 750 899;
terpolymers comprising from 10 mol % to 90 mol % of acrylamide units, from 0.1 mol % to 10 mol % of AMPS units and from 5 mol % to 80 mol % of n($C_6$-$C_{18}$)alkylacrylamide units relative to the polymer, such as those described in U.S. Pat. No. 5,089,578.

As amphiphilic polymers that are suitable for use in the invention, mention may be made of polyoxyethylenated (crosslinked or noncrosslinked) copolymers of AMPS® and of alkyl methacrylates, and mixtures thereof.

As amphiphilic polymers that are suitable for use in the invention, mention may also be made of copolymers of totally neutralized AMPS® and of n-dodecyl, n-hexadecyl and/or n-octadecyl methacrylate, and also copolymers of AMPS and of n-dodecylmethacrylamide, which may be crosslinked or noncrosslinked.

Mention may also be made of crosslinked or non-crosslinked amphiphilic copolymers comprising, or even formed from:
2-acrylamido-2-methylpropanesulfonic acid (AMPS®) units of formula (2) below:

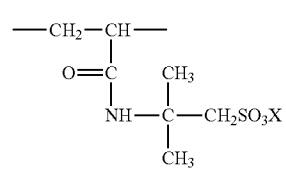

(2)

in which X may be a proton, an alkali metal cation, an alkaline-earth metal cation or an ammonium ion;
and units of formula (3) below:

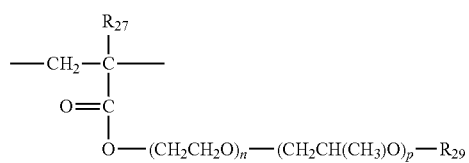

(3)

in which:
n and p, independently of each other, denote a number of moles and range from 0 to 30, in particular from 1 to 25 and more particularly from 3 to 20, with the proviso that n+p is less than or equal to 30, in particular less than 25 and more particularly less than 20;
$R_{27}$ has the same meaning indicated in the preceding formula (1), and
$R_{29}$ denotes a linear or branched alkyl radical comprising m carbon atoms, m ranging from 7 to 22 and preferably from 12 to 20.
In formula (2), the cation X may more particularly denote sodium or ammonium.

Mention may be made in particular of:
noncrosslinked polymers for which p=0, n=7 or 25, $R_{27}$ denotes methyl and $R_{29}$ represents a mixture of $C_{12}$-$C_{14}$ or $C_{16}$-$C_{18}$ alkyl, and
crosslinked polymers for which p=0, n=8 or 25, $R_{27}$ denotes methyl and $R_{29}$ represents a mixture of $C_{16}$-$C_{18}$ alkyl.

These polymers are described and synthesized in document EP 1 069 142.

These particular amphiphilic polymers may be obtained according to the standard free-radical polymerization processes in the presence of one or more initiators such as, for example, azobisisobutyronitrile (AIBN), azobisdimethylvaleronitrile, 2,2-azobis[2-amidinopropane]hydrochloride (ABAH), organic peroxides such as dilauryl peroxide, benzoyl peroxide, tert-butyl hydroperoxide, etc., mineral peroxide compounds such as potassium persulfate or ammonium persulfate, or $H_2O_2$ optionally in the presence of reducing agents.

These amphiphilic polymers may be obtained by free-radical polymerization in tert-butanol medium, in which they precipitate.

By using precipitation polymerization in tert-butanol, it is possible to obtain a size distribution of the polymer particles that is particularly favorable for its uses.

The reaction may be performed at a temperature of between 0 and 150° C. and preferably between 10 and 100° C., either at atmospheric pressure or under reduced pressure.

The reaction may also be performed under inert atmosphere, and preferably under nitrogen.

A polymer in accordance with the invention may be partially or totally neutralized with a mineral or organic base such as those mentioned above.

The molar percentage concentration of the units of formula (2) and of the units of formula (3) in an amphiphilic polymer according to the invention may vary as a function of the desired cosmetic application, the nature of the emulsion (oil-in-water or water-in-oil emulsion) and the rheological properties of the desired formulation.

It can range between 0.1 and 99.9 mol %.

The molar proportion of units of formula (3) in an amphiphilic polymer according to the invention may preferably range from 0.1% to 50%, more particularly from 1% to 25% and even more particularly from 3% to 10%.

The molar proportion of units of formula (3) in an amphiphilic polymer according to the invention may preferably range from 50.1% to 99.9%, more particularly from 60% to 95% and even more particularly from 65% to 90%.

The distribution of the monomers in the polymers of the invention may be, for example, alternate, block (including multiblock) or random.

As a guide, and without this being limiting, mention may be made of the following commercial references: Aristoflex® HMS and Aristoflex® HMB sold by Clariant, these two references relating to crosslinked polymers.

Aristoflex® HMS is the name of the AMPS®/ethoxylated (25 EO) cetearyl methacrylate copolymer 80/20, crosslinked with trimethylolpropane triacrylate (TMPTA) or ammonium acryloyldimethyltaurate/stearate-25 methacrylate crosspolymer as the INCI name.

As the INCI name, Aristoflex® HMB is ammonium acryloyldimethyltaurate/Beheneth-25 methacrylate crosspolymer.

It is also possible to use, as hydrophobic AMPS copolymer, noncrosslinked AMPS® copolymers (Aristoflex® LNC or SNC), which are also effective in terms of stabilizing emulsions.

As the INCI name, Aristoflex® LNC is ammonium acryloyldimethyltaurate/Laureth-7 methacrylate copolymer.

As the INCI name, Aristoflex® SNC is ammonium acryloyldimethyltaurate/Steareth-8 methacrylate copolymer.

Among the acrylic polymers that may be combined with a combination in accordance with the invention, mention may also be made of neutralized crosslinked acrylic homopolymers or copolymers.

c—Neutralized Crosslinked Acrylic Homopolymers or Copolymers

All crosslinked acrylic homopolymers or copolymers are suitable for use in the present invention provided that they are used in an at least partially neutralized form.

As regards these crosslinked acrylic polymers already neutralized before use, or otherwise, examples that may be mentioned include:

Cosmedia SP® or crosslinked sodium polyacrylate containing 90% solids and 10% water, Cosmedia SPL® or sodium polyacrylate as an inverse emulsion containing about 60% dry active material, an oil (hydrogenated polydecene) and a surfactant (PPG-5 laureth-5), both sold by the company Cognis, modified or unmodified carboxyvinyl polymers (for instance optionally crosslinked acrylic acid polymers), such as the products sold under the names Carbopol (INCI name: Carbomer) by the company Goodrich, partially neutralized crosslinked sodium polyacrylates that are in the form of an inverse emulsion comprising at least one polar oil, for example the product sold under the name Luvigel® EM sold by the company BASF, and mixtures thereof.

A preferred hydrophilic gelling agent of the present invention is ammonium polyacryloyldimethyl taurate, also known under the tradename, Hostacerin AMPS®, and commercially available from the supplier Clariant. It is also described as polyacrylamidomethylpropane sulfonic acid (AMPS®) partially neutralized with ammonia and highly cross-linked.

Other preferred hydrophilic gelling agents of the present invention are:

AMPS® and acrylamide copolymers of the Sepigel® or Simulgel® type sold by the supplier Seppic; and copolymers of AMPS® and polyoxyethylene alkyl methacrylates (optionally cross-linked), and mixtures thereof such as ammonium acryloyldimethyltaurate/steareth-25 methacrylate crosspolymer, available under the tradenames Aristoflex HMS; ammonium acryloyldimethyltaurate/steareth-8 methacrylate crosspolymer, available under the tradenames Aristoflex SNC; and ammonium acryloyldimethyltaurate/VP copolymer, available under the tradenames Aristoflex AVC, Aristoflex JQD, Hostacerin SAF, all commercially available from the supplier Clariant;

The at least one hydrophilic gelling agent(s) may be present in the cosmetic composition in an amount ranging from about 0.01% to about 5% by weight, such as from about 0.1% to about 3% by weight, or from about 0.25% to about 2% by weight, relative to the total weight of the cosmetic composition, including all ranges and subranges therebetween. In other embodiments, the at least one hydrophilic gelling agent(s) may be present in an amount of about 2% by weight, or about 1% by weight, or about 0.5% by weight, relative to the total weight of the cosmetic composition.

The at least one hydrophilic gelling agent is preferably soluble in water or in the aqueous phase of the present invention.

Aqueous Phase

The compositions of the present invention also comprise an aqueous phase. The aqueous phase of the composition according to the invention is advantageously a continuous aqueous phase.

The term "composition with a continuous aqueous phase" means that the composition has a conductivity, measured at 25° C., of greater than 23 μS/cm (microSiemens/cm), the conductivity being measured, for example, using an MPC227 conductimeter from Mettler Toledo and an Inlab730 conductivity measuring cell. The measuring cell is immersed in the composition so as to remove any air bubbles liable to form between the two electrodes of the cell. The conductivity reading is taken once the conductimeter value has stabilized. A mean is determined over at least three successive measurements.

The continuous aqueous phase of the composition according to the invention comprises water and/or at least one water-soluble solvent.

In the present invention, the term "water-soluble solvent" denotes a compound that is liquid at room temperature and water-miscible (miscibility in water of greater than 50% by weight at 25° C. and atmospheric pressure).

The water-soluble solvents that may be used in the compositions according to the invention may also be volatile.

Among the water-soluble solvents that may be used in the compositions according to the invention, mention may be made especially of lower monoalcohols containing from 1 to 5 carbon atoms, such as ethanol and isopropanol, glycols containing from 2 to 8 carbon atoms, such as ethylene glycol, propylene glycol, 1,3-butylene glycol and dipropylene glycol, $C_3$ and $C_4$ ketones and $C_2$-$C_4$ aldehydes.

The aqueous phase is present in the cosmetic composition of the present invention in an amount from about 5% to about 95% by weight, and in preferred embodiments, from about 20% to about 80% by weight, and in other preferred embodiments, from about 20% to about 60% by weight, or from about 20% to about 50% by weight, or from about 20% to about 40% by weight, relative to the total weight of the cosmetic composition.

In some embodiments, the aqueous phase contains at least 20% by weight of water, relative to the total weight of the cosmetic composition.

In other embodiments, the aqueous phase contains at least 20% by weight of water and up to 60% by weight of at least one organic solvent, relative to the total weight of the cosmetic composition.

Emulsifying System

The composition according to the invention may contain traditional emulsifiers and co-emulsifiers such as surfactants especially present in a proportion ranging from 0.1% to 30%, or from 1% to 15% and or from 2% to 10% by weight relative to the total weight of the composition.

According to the invention, the emulsifiers and co-emulsifiers are appropriately chosen in order to obtain an oil-in-water emulsion. In particular, an emulsifier having at 25° C. an HLB (hydrophilic-lipophilic balance) of greater than or equal to 8 may be used.

These surfactants may be chosen from nonionic, anionic, cationic and amphoteric surfactants or combinations thereof.

The surfactants are preferably chosen from nonionic ethoxylated fatty alcohols and fatty alcohols.

In certain preferred embodiments of the present invention, the emulsifying system of the present invention does not employ a traditional emulsifier. In such embodiments, the emulsifying system may employ an amino acid, such as arginine, in combination with a fatty acid, such as stearic acid. Arginine may also function to provide additional benefits to the eyelashes.

Liquid Fatty Phase

The composition according to the invention may comprise a fatty phase that is liquid at room temperature (25° C.) and atmospheric pressure (760 mmHg), composed of one or more mutually compatible non-aqueous fatty substances that are liquid at room temperature, also known as organic solvents or oils.

The oil may be chosen from volatile oils and/or non-volatile oils, and mixtures thereof.

Representative solvents of the present invention include non-polar volatile hydrocarbon-based oils (which as used herein, refers to oil containing only hydrogen and carbon atoms.

Suitable hydrocarbon-based oils include isoparaffins, i.e., branched alkanes containing 8-16 carbon atoms, such as isododecane (also known as 2,2,4,4,6-pentamethylheptane), isodecane, and for example, the oils sold under the trade names of Isopar™ or Permethyl®. Preferably, the volatile non-silicone oils have a flash point of at least 40 degrees centigrade.

Non-limiting examples of volatile non-silicone volatile oils are given below:

| Compound | Flash Point (° C.) |
|---|---|
| Isododecane | 43 |
| propylene glycol n-butyl ether | 60 |
| ethyl 3-ethoxypropionate | 58 |
| propylene glycol methylether acetate | 46 |
| Isopar ™ L (isoparaffin C11-C13) | 62 |
| and Isopar ™ H (isoparaffin C11-C12) | 56 |

The volatility of the solvents/oils can be determined using the evaporation speed as set forth in U.S. Pat. No. 6,338,839, the contents of which are incorporated by reference herein.

Other exemplary organic solvents are non-polar non-volatile solvents including polyalphaolefins, which include ethylene derivatives oligomerized into even-numbered carbon polyalphaolefins e.g., C6-C14 olefins such as polydecene and polymers of C6, C8, C12 and C14 olefins. The polyolefins may have a molecular weight (MW) generally ranging from about 280 to about 11,500, and a viscosity (CPs at 20 degrees C.) generally ranging from about 7 to about 32,500. They may also be hydrogenated. In some embodiments, the non-volatile solvent includes PureSyn™2 (MW about 283), 4 (MW about 432), 6 (MW about 570), 8 (MW about 611), 150 (MW about 3980) and 300 (MW about 4870) (INCI name: hydrogenated polydecene). The viscosity of these polymers is about 8, about 33, about 64, about 103, about 4179 and about 8400, respectively) PureSyn™100 (MW about 2939, viscosity about 3900, INCI name: hydrogenated C6-14 olefin polymers) and PureSyn™1000 (MW about 11,500, viscosity about 32,400, INCI name: polydecene) may also be useful. The PureSyn™ products are available from Exxon Chemicals.

The non-volatile solvent is present in the cosmetic composition of the present invention in an amount generally ranging from about 0.1% to about 70% by weight, and in some embodiments, about 0.5% to about 40% by weight, and in other embodiments, about 1% to about 10% by weight, relative to the total weight of the cosmetic composition.

The inventive compositions may contain any other cosmetically or dermatologically acceptable and, in general, physiologically acceptable oil, such as carbon-based, hydrocarbon-based, fluoro and/or silicone oils, of mineral, animal, plant or synthetic origin, alone or as a mixture. These ingredients, along with the non-polar solvents, could comprise the liquid fatty phase or oil carrier of the cosmetic composition of the present invention. According to other embodiments of the present invention, the oil carrier comprises at least one non-volatile oil. Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol® 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, C12 to C15 alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

C8 to C26 fatty alcohols, for instance oleyl alcohol, cetyl alcohol, stearyl alcohol, and cetearyl alcohol; and mixtures thereof.

Further, examples of non-volatile oils that may be used in the present invention include, but are not limited to, non-polar oils such as branched and unbranched hydrocarbons and hydrocarbon waxes including polyolefins, in particular, Vaseline (petrolatum), paraffin oil, squalane, squalene, hydrogenated polyisobutene, hydrogenated polydecene, polybutene, mineral oil, pentahydrosqualene, and mixtures thereof.

Suitable silicone oils may include linear or cyclic silicones containing from 2 to 7 silicon atoms, these silicones optionally comprising alkyl or alkoxy groups containing from 1 to 10 carbon atoms. Mention may thus be made especially of octamethylcyclotetrasiloxane, decamethylcyclopentasiloxane, hexadecamethylcyclohexasiloxane, heptamethylhexyltrisiloxane hexamethyldisiloxane, decamethyltetrasiloxane, dodecamethylpentasiloxane, heptamethyloctyltrisiloxane, decamethyltetrasiloxane, and their mixtures. Other volatile oils which may be used include KF 96A of 6 cSt viscosity, a commercial product from Shin Etsu having a flash point of 94 degrees centigrade and polydimethylsiloxanes (PDMS) such as those available from Dow Corning under the tradename DC® 200. Preferably, the volatile silicone oils have a flash point of at least 40 degrees centigrade, and mixtures thereof. Mixtures of these solvents may be used.

Waxes

The cosmetic composition of the present invention may further comprise at least one wax.

For the purposes of the present invention, the term "wax" is understood to mean a lipophilic compound, which is solid at room temperature (25 degrees C.), with a reversible solid/liquid change of state, which has a melting point of greater than or equal to 30 degrees C., which may range up to 120.degrees C.

The melting point of the wax may be measured using a differential scanning calorimeter (DSC), for example the calorimeter sold under the name DSC 30 by Mettler. For waxes that are derived from petroleum, such as microcrystalline wax, the melting point may be measured according to the drop ASTM method, D-127.

The waxes may be hydrocarbon-based waxes, fluoro waxes and/or silicone waxes and may be of plant, mineral, animal and/or synthetic origin. In particular, the waxes have a melting point of greater than 25 degrees C. and better still greater than 45 degrees C.

Hydrocarbon-based waxes, for instance beeswax, lanolin wax or Chinese insect wax; rice wax, carnauba wax, candelilla wax, ouricury wax, esparto grass wax, cork fibre wax, sugarcane wax, Japan wax and sumach wax; montan wax, microcrystalline waxes, paraffins and ozokerite, polyethylene waxes, the waxes obtained by Fisher-Tropsch synthesis and waxy copolymers, and also esters thereof, may especially be used.

Mention may also be made of waxes obtained by catalytic hydrogenation of animal or plant oils containing linear or branched C8-C32 fatty chains.

Among these waxes, mention may especially be made of hydrogenated jojoba oil, isomerized jojoba oil such as the trans-isomerized partially hydrogenated jojoba oil manufactured or sold by Desert Whale under the commercial reference ISO-JOJOBA-50®, hydrogenated sunflower oil, hydrogenated castor oil, hydrogenated coconut oil, hydrogenated lanolin oil, bis(1,1,1-trimethylolpropane)tetrastearate sold under the name HEST 2T-4S® by Heterene and bis(1,1,1-trimethylol-propane)tetrabehenate sold under the name HEST 2T-4B® by Heterene.

Mention may also be made of silicone waxes, for instance alkyl or alkoxy dimeticones containing from 16 to 45 carbon atoms, and fluoro waxes.

The wax obtained by hydrogenation of olive oil esterified with stearyl alcohol, sold under the name PHYTOWAX® OLIVE 18L57 or else the waxes obtained by hydrogenation of castor oil esterified with cetyl alcohol sold under the names PHYTOWAX® RICIN 16L64 and 22L73 by Sophim may also be used. Such waxes are described in patent application FR-A-2 792 190.

The at least one wax of the present invention may also be a polar wax. The expression "polar wax" is understood to mean waxes comprising in their chemical structure, in addition to carbon and hydrogen atoms, at least one highly electronegative heteroatom, such as O, N or P.

The at least one wax of the present invention may also be chosen from silicone waxes and siloxane resin waxes (also known as silsesquioxane resin waxes).

A suitable example of a silsesquioxane resin wax is a propylsilsesquioxane wax substituted with alkyl units having from 9-40 carbon atoms, preferably, at least 30 carbon atoms.

Propylsilsesquioxane waxes, in general, have been disclosed in patent publication WO2005/100444, published on Oct. 27, 2005.

The propylsilsesquioxane wax comprises at least 40 mole % of siloxy units having the formula (R2R'SiO1/2)x (C3H7SiO3/2)y, where x and y have a value of 0.05 to 0.95, R is an alkyl group having from 1 to 8 carbon atoms, and R' is a monovalent hydrocarbon having 30 to 40 carbon atoms and greater. As used herein, x and y represent the mole fraction of (R2R'SiO1/2) and (C3H7SiO3/2) siloxy units relative to each other present in the propylsilsesquioxane wax. Thus, the mole fraction of (R2R'SiO1/2) and (C3H7SiO3/2) siloxy units each can independently vary from 0.05 to 0.95. Preferably R is a methyl, and R' is an alkyl having at least 30 carbons, available from Dow Corning.

Typically, the value of x is 0.05 to 0.95, or alternatively, 0.2 to 0.8, the value of y is 0.05 to 0.95, alternatively 0.2 to 0.8. However, the combination of (R2R'SiO1/2) and (C3H7SiO3/2) siloxy units present must total at least 40 mole %, alternatively 60 mole %, or alternatively 90 mole % of all siloxy units present in the propylsilsesquioxane wax.

The number average molecular weight of the propylsilsesquioxane wax substituted with alkyl units having at least 30 carbons typically ranges from about 750 to about 10,000, such as from about 1,000 to about 5,000.

The propylsilsesquioxane wax substituted with alkyl units having at least 30 carbons is commercially available under the INCI name C30-45 Alkyldimethylsilyl polypropylsilsesquioxane and trade name SW-8005 C30 resin wax from the supplier Dow Corning.

Preferably, the at least one wax of the present invention is chosen from carnauba wax, candelilla wax, natural (or bleached) beeswax, synthetic beeswax, paraffin wax, silicone waxes, and silsesquioxane resin waxes. As synthetic beeswax, mention may be made of the wax sold under the name CYCLOCHEM® 326 A by Evonik Goldschmidt (INCI name: Synthetic Beeswax).

The composition may comprise at least one wax having a hardness ranging from 0.05 MPa to 15 MPa, and preferably ranging from 6 MPa to 15 MPa. The hardness is determined by measuring the compression force, which is measured at 20 degrees C. using the texturometer sold under the name TA-TX21® by Rheo, equipped with a stainless-steel cylinder 2 mm in diameter, travelling at a measuring speed of 0.1 mm/s, and penetrating into the wax to a penetration depth of 0.3 mm.

According to one particular embodiment, the compositions according to the invention may comprise at least one wax referred to as a tacky wax, i.e. a wax with a tack of greater than or equal to 0.7 N·s and a hardness of less than or equal to 3.5 MPa Using a tacky wax may especially make it possible to obtain a cosmetic composition that applies easily to the eyelashes, attaches well to the eyelashes and leads to the formation of a smooth, uniform and thickening makeup result.

The tacky wax used may especially have a tack ranging from 0.7 N·s to 30 N·s, in particular greater than or equal to 1 N·s, especially ranging from 1 N·s to 20 N·s, in particular greater than or equal to 2N·s, especially ranging from 2 N·s to 10N·s and in particular ranging from 2 N·s to 5 N·s.

The tack of the wax is determined by measuring the change in force (compression force or stretching force) as a function of time, at 20 degrees C., using the texturometer sold under the name TA-TX2i® by Rheo, equipped with a conical acrylic polymer spindle forming an angle of 45 degrees.

The measuring protocol is as follows:

The wax is melted at a temperature equal to the melting point of the wax +10 degree C. The molten wax is poured into a container 25 mm in diameter and 20 mm deep. The wax is recrystallized at room temperature (25 degrees C.) for 24 hours such that the surface of the wax is flat and smooth, and the wax is then stored for at least 1 hour at 20 degrees C. before measuring the tack.

The texturometer spindle is displaced at a speed of 0.5 mm/s then penetrates the wax to a penetration depth of 2 mm. When the spindle has penetrated the wax to a depth of 2 mm, the spindle is held still for 1 second (corresponding to the relaxation time) and is then withdrawn at a speed of 0.5 mm/s.

During the relaxation time, the force (compression force) decreases greatly until it becomes zero, and then, during the withdrawal of the spindle, the force (stretching force) becomes negative and then rises again to the value 0. The tack corresponds to the integral of the curve of the force as a function of time for the part of the curve corresponding to negative values of the force (stretching force). The tack value is expressed in N·s.

The tacky wax that may be used generally has a hardness of less than or equal to 3.5 MPa, in particular ranging from 0.01 MPa to 3.5 MPa, especially ranging from 0.05 MPa to 3 MPa or even ranging from 0.1 MPa to 2.5 MPa.

The hardness is measured according to the protocol described previously.

Tacky waxes that may be used include a C20-C40 alkyl (hydroxystearyloxy)stearate (the alkyl group comprising from 20 to 40 carbon atoms), alone or as a mixture, in particular a C20-C40 alkyl 12-(12'-hydroxystearyloxy)stearate, Such a wax is especially sold under the names KESTER WAX K 82 P® and KESTER WAX K 80 P® by Koster Keunen.

For waxes that are derived from petroleum, such as microcrystalline wax, the hardness may be measured according to the ASTM method for needle penetration of petroleum waxes, D-1321 @100/77/5. This method employs a penetrometer which measures the consistency or hardness of a semiliquid to semisolid material based on the penetration force and depth at which a cone or needle goes into the material. A penetration value of 80 corresponds to a penetration depth of 8.0 mm.

The at least one microcrystalline wax that may be used in the composition of the present invention may be chosen from the microcrystalline waxes sold by the company Strahl and Pitsch under a reference S&P number, such as SP96, SP18, SP19, SP26, SP60W, SP60, SP16, SP617, SP89 and SP624 (referred to herein as "SP microcrystalline waxes"). The melting points of the SP microcrystalline waxes are measured according to the drop ASTM method, D-127. The penetration hardness values of the SP microcrystalline waxes are determined according to the ASTM method, D-1321 @100/77/5.

The waxes mentioned above generally have a starting melting point of less than 45 degree C.

The at least one wax of the present invention may be present in the form of an aqueous microdispersion of wax. The expression "aqueous microdispersion of wax" is understood to mean an aqueous dispersion of wax particles in which the size of said wax particles may range from less than 1 micron to 100 microns.

These particles are essentially constituted of a wax or a mixture of waxes. However, they may comprise a small proportion of oily and/or pasty fatty additives, a surfactant and/or a common liposoluble additive/active agent.

The at least one wax may be present in the cosmetic composition in an amount ranging from greater than 0% to about 40% by weight, such as from about 5% to about 40% by weight, or from about 5% to about 30% by weight, or from about 10% to about 25% by weight, or from about 15% to about 25% by weight, relative to the total weight of the cosmetic composition, including all ranges and subranges therebetween.

In preferred embodiments, the at least one wax will be present in the cosmetic composition in an amount less than or equal to 25% by weight, less than or equal to 20% by weight, or less than or equal to 19% by weight, less than or equal to 18% by weight relative to the total weight of the cosmetic composition.

Desired Agents

According to preferred embodiments of the present invention, the compositions can further comprise a desired agent. The desired agent can be, for example, a colorant (pigment, dye, etc.), a fiber, a cosmetically active agent, a film forming agent or a gelling agent other than the at least one hydrophilic gelling agent described above. For example, a cosmetic makeup composition of the present invention and further comprising a colorant can provide a desired color to a substrate (eyelashed, eyebrows, etc.) during use. Similarly, the cosmetic composition of the present invention further comprising a cosmetically active agent can provide such active agent to the consumer upon use.

Acceptable colorants include pigments, dyes, such as liposoluble dyes, nacreous pigments, and pearling agents.

Representative liposoluble dyes which may be used according to the present invention include Sudan Red, DC® Red 17, DC® Green 6, beta-carotene, soybean oil, Sudan Brown, DC® Yellow 11, DC® Violet 2, DC® Orange 5, annatto, and quinoline yellow.

Representative nacreous pigments include white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride.

Representative pigments include white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D and C type, and lakes based on cochineal carmine, and barium.

Suitable fibers include, but are not limited to, fibers which enable improvement of the thickening/volumizing and/or lengthening effect. As used herein, the term "fiber" is understood to mean an object of length L and diameter D such that L is greater than D, for instance, L may be very much greater than D, wherein D is the diameter of the circle in which the cross section of the fiber is inscribed. For example, the ratio of L to D (or shape factor) can range from 3.5 to 2,500, for instance, from 5 to 500, such as from 5 to 150.

The fibers that can be used in the composition of the present disclosure may be mineral or organic fibers of synthetic or natural origin. They may be short or long, individual or organized, for example braided, and hollow or solid. They may have any shape, and may have, for example, a circular or polygonal (square, hexagonal or octagonal) cross section, depending on the intended specific application. In one embodiment of the present disclosure, the fibers' ends are blunt and/or polished to prevent injury.

For example, the fibers can have a length ranging from 1 mu m to 10 mm, for instance from 0.1 mm to 5 mm, such as from 0.3 mm to 3 mm. Their cross section may be within a circle of diameter ranging from 2 nm to 500 mu m, for instance ranging from 100 nm to 100 mu m, such as from 1 mu m to 50 mu m. The weight or yarn count of the fibers is often given in denier or decitex, and represents the weight in grams per 9 km of yarn. For example, the fibers according to the present disclosure may have a yarn count ranging from 0.01 denier to 10 denier, for instance from 0.1 denier to 2 denier, such as from 0.3 denier to 0.7 denier.

The fibers that can be used include those used in the manufacture of textiles, such as silk fiber, cotton fiber, wool fiber, flax fiber, cellulose fiber extracted for instance, from wood, from legumes or from algae, rayon fiber, polyamide (Nylon) fiber, viscose fiber, acetate fiber, such as rayon acetate fiber, acrylic polymer fiber, for instance: polymethyl methacrylate fiber or poly(2-hydroxyethyl methacrylate) fiber, polyolefin fiber such as polyethylene or polypropylene fiber, glass fiber, silica fiber, carbon fiber, for instance in graphite form, polytetrafluoroethylene (such as Teflon) fiber, insoluble collagen fiber, polyester fiber, polyvinyl chloride fiber or polyvinylidene chloride fiber, polyvinyl alcohol fiber, polyacrylonitrile fiber, chitosan fiber, polyurethane fiber, polyethylene phthalate fiber, and fibers formed from a mixture of polymers such as those mentioned above, for instance polyamide/polyester fibers.

In one embodiment of the present disclosure, the fibers are polyamide (Nylon) fibers.

The fibers used in surgery can also be used, for instance the resorbable synthetic fibers prepared from glycolic acid and caprolactone (Monocryl from Johnson Johnson); resorbable synthetic fibers of the type which is a copolymer of lactic acid and of glycolic acid (Vicryl from Johnson Johnson); polyterephthalic ester fibers (Ethibond from Johnson Johnson) and stainless steel threads (Acier from Johnson Johnson).

Moreover, the fibers may or may not be surface-treated, and may or may not be coated with a protective coat. Among coated fibers that may be used as disclosed herein, non-limiting mention may be made of polyamide fibers coated with copper sulphide to give an anti-static effect (for example R-STAT from Rhodia) or another polymer enabling a particular organization of the fibers (specific surface treatment). Non-limiting mention may also be made of fibers coated with mineral or organic pigments, such as the pigments described herein below.

For example, in another embodiment of the present disclosure, fibers of synthetic origin, for instance organic fibers, such as those used in surgery, are used.

For further example, in still another embodiment of the present disclosure, the fibers may be chosen from polyamide fibers, cellulose fibers and polyethylene fibers. Their length (L) may range from 0.1 mm to 5 mm such as from 0.25 mm to 1.6 mm, and their mean diameter may range from 1 mu m to 50 mu m. For instance, the polyamide fibers sold by Etablissements P. Bonte under the name "Polyamide 0.9 Dtex 3 mm," having a mean diameter of 6 mu m, a yarn count of about 0.9 dtex and a length ranging from 0.3 mm to 5 mm, or the polyamide fibers sold under the name Fiberlon 931-D1-S by the company LCW, having a yarn count of about 0.9 dtex and a length of about 0.3 mm, may be used. Cellulose (or rayon) fibers with a mean diameter of 50 mu m and a length ranging from 0.5 mm to 6 mm may also be used, for instance those sold under the name "Natural rayon flock fiber RC1BE-N003-M04" by the company Claremont Flock. Polyethylene fibers, for instance those sold under the name "Shurt Stuff 13 099 F" by the company Mini Fibers, may also be used.

Elastomeric fibers may also be used, i.e. fibers which, when subjected to a stretching stress (for example of 30 percent relative to their initial length), return to a length substantially identical to their initial length when the stress is removed. Among the elastomeric fibers that may be used, non-limiting mention may be made of polyurethane fibers such as elastane (or Spandex®), fibers comprising at least 85 percent by weight of segmented polyurethane, such as Lycra® sold by Dupont de Nemours, elastodiene, or alternatively rubbery fibers obtained from natural rubber. These elastomeric fibers may or may not be vulcanized.

The composition according to the present disclosure may also comprise "rigid" fibers, as opposed to the fibers mentioned above, which are not rigid fibers.

The rigid fibers, which are initially substantially straight, when placed in a dispersing medium, do not undergo a substantial change in shape, which is reflected by the angular condition defined below, reflecting a shape that may be described as still substantially straight and linear. This angle condition reflects the stiffness of the fibers, which it is difficult to express by another parameter for objects that are as small as the rigid fibers.

The stiffness of the fibers is reflected by the following angular condition: for example, at least 50 percent, for instance at least 75 percent, such as at least 90 percent, in numerical terms, of the rigid fibers are such that the angle formed between the tangent to the longitudinal central axis of the fiber and the straight line connecting the said end to the point on the longitudinal central axis of the fiber corresponding to half the length of the fiber is less than 15 degrees, and the angle formed between the tangent to the longitudinal central axis of the fiber at a point half way along the fiber and the straight line connecting one of the ends to the point on the longitudinal central axis of the fiber corresponding to half the length of the fiber, is less than or equal to 15 degrees for the same fiber length ranging from 0.8 mm to 5 mm, for instance ranging from 1 mm to 4 mm, and from 1 mm to 3 mm, such as 2 mm.

For example, the angle mentioned above may be measured at the two ends of the fiber and at a point half way along the fiber; in other words, three measurements can be taken in this case and the average of the measured angles is less than or equal to 15 degrees.

The tangent, at any point on the fiber, for instance forms an angle of less than 15 degrees.

In the present disclosure, the angle formed by the tangent at a point on the fiber is the angle formed between the tangent to the longitudinal central axis of the fiber at the said point on the fiber and the straight line connecting the end of the fiber that is closest to the said point to the point on the longitudinal central axis of the fiber corresponding to half the length of the fiber.

For example, the rigid fibers that may be used in the composition as disclosed herein can have the same or substantially the same fiber length.

For instance, when a medium where rigid fibers are dispersed in an amount of 1 percent by weight, is observed by microscope, with an objective lens allowing a magnification of 2.5 and with full-field vision, a numerical majority of the rigid fibers, i.e. at least 50 percent numerically of the rigid fibers, for instance, at least 75 percent numerically of the rigid fibers such as at least 90 percent numerically of the rigid fibers, must satisfy the angular condition defined above. The measurement leading to the angle value is performed for the same length of fibers, this length ranging from 0.8 mm to 5 mm, for instance from 1 to 4 mm, and from 1 to 3 mm, such as 2 mm.

The medium on which the observation is performed is a dispersing medium that ensures good dispersion of the rigid fibers, for example water or an aqueous gel of clay or of associative polyurethane. A direct observation of the composition comprising the rigid fibers may even be performed. A sample of the prepared composition or dispersion is placed between a slide and cover slip for observation by microscope with an objective lens allowing a magnification of 2.5 and with full-field vision. Full-field vision allows the fibers to be viewed in their entirety.

The rigid fibers can be chosen from fibers of a synthetic polymer chosen from polyesters, polyurethanes, acrylic polymers, polyolefins, polyamides, for instance nonaromatic polyamides, and aromatic polyimideamides.

Non-limiting examples of rigid fibers that may be mentioned include:

polyester fibers, such as those obtained by chopping yarns sold under the names Fiber 255-100-R11-242T Taille 3 mm (eight-lobed cross section), Fiber 265-34-R11-56T Taille 3 mm (round cross section) and Fiber Coolmax 50-34-591 Taille 3 mm (four-lobed cross section) by the company Dupont de Nemours;

polyamide fibers, such as those sold under the names Trilobal Nylon® 0.120-1.8 DPF; Trilobal Nylon® 0.120-18 DPF; Nylon® 0.120-6 DPF by the company Cellusuede products; or obtained by chopping yarns sold under the name Fiber Nomex® Brand 430 Taille 3 mm by the company Dupont de Nemours;

polyimideamide fibers, such as those sold under the names "Kermel®" and "Kermel Tech®" by the company RHODIA;

poly(p-phenyleneterephthalamide) (or aramide) sold, for instance, under the name Kevlar® by the company Dupont de Nemours;

fibers with a multilayer structure comprising alternating layers of polymers chosen from polyesters, acrylic polymers and polyamides. Such fibers are sold under the names "Morphotex®" and "Teijin Tetron Morphotex®" by the company Teijin.

In one embodiment of the present disclosure, the rigid fibers are chosen from aromatic polyimideamide fibers.

In one aspect of the present disclosure, the aromatic polyimideamide fibers are polyimideamide fibers comprising repeating units of formula:

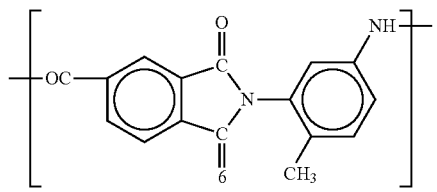

obtained by polycondensation of tolylene diisocyanate and trimellitic anhydride.

The fibers are present in the composition according to the present disclosure in an amount ranging from 0.05 percent to 10 percent by weight, for instance from 0.1 percent to 5 percent by weight, such as from 0.3 percent to 3 percent by weight, relative to the total weight of the composition.

The film forming agent that may be used in the compositions of the present disclosure may be chosen from hydrocarbon film forming polymers, silicone film forming polymers, vinyl polymers, silicone polyamides, linear film forming ethylenic block copolymers, acrylate polymers, hydrolyzed corn starch, and latex polymers. The film forming agent may be either water-soluble or lipo-soluble.

Preferably, the hydrocarbon film forming polymer is soluble in a volatile solvent.

Advantageously, the hydrocarbon film forming polymer is a hydrocarbon "tackifier" resin.

Said hydrocarbon film forming polymer is preferably an olefin polymer or copolymer or an aromatic hydrocarbon monomer polymer or copolymer, preferably an indene hydrocarbon resin, e.g. as described below. Said hydrocarbon film forming polymer may be hydrogenated, partially hydrogenated, or non-hydrogenated.

Preferably, said hydrocarbon film forming polymer presents a softening point that is less than 120 degrees centigrade, preferably less than 110 degrees centigrade.

In the context of the present invention, the softening point is measured using the ring-and-ball method in accordance with the ASTM D36 Standard. To do this, use is made of an automatic NBA 440 tester available from Normalab. The fluid used for the measurement is glycerin.

The hydrocarbon resins of the invention are selected from polymers that may, depending on the type of monomer that they contain, be classified as:

(a) indene hydrocarbon resins such as the resins derived from the polymerization of indene monomer in the greater proportion, and of a monomer selected from styrene, methylindene, methylstyrene, and mixtures thereof in the lesser proportion. These resins may possibly be hydrogenated. They may present a molecular weight lying in the range 290 grams per mole (g/mol) to 1150 g/mol;

Examples of indene resins that may be mentioned are those sold under the reference NORSOLENE®® S95, NORSOLENE®® S105, NORSOLENE®® 5115 by the Supplier Cray Valley, or hydrogenated indene/methylstyrene/styrene copolymers sold under the name "REGALITE™" by the supplier Eastman Chemical, in particular REGALITE™

C6100, REGALITE™ C6100L, REGALITE™ R1090, REGALITE™ R1100, REGALITE™ R7100, REGALITE™ R9100, REGALITE™ S1100, REGALITE™ S5100, or under the name ARKON® P-90, ARKON® P-100, ARKON® P-115, ARKON® M-90, ARKON® M-100, ARKON® M-115 by the supplier Arakawa.

(b) aliphatic pentadiene resins such as that derived from the polymerization mainly of 1,3-pentanediene (trans or cis piperylene) and of a minor monomer selected from isoprene, butene, 2-methyl-2-butene, pentene, 1,4-pentadiene and mixtures thereof. These resins may present a molecular weight lying in the range 1000 g/mol to 2500 g/mol.

By way of example, such 1,3-pentadiene resins are sold under the references PICCOTAC™ 95 by the supplier Eastman Chemical, ESCOREZ® 1102, ESCOREZ® 1304, ESCOREZ® 1310LC, ESCOREZ® 1315 by the supplier Exxon Chemicals, WINGTACK® 95 by the supplier Cray Valley;

(c) mixed pentadiene and indene resins that are derived from the polymerization of a mixture of pentadiene and indene monomers such as those described above, such as for example the resins sold under the reference ESCOREZ® 2101, ESCOREZ® 2105, ESCOREZ® 2173, ESCOREZ® 2184, ESCOREZ® 2203LC, ESCOREZ® 2394, ESCOREZ® 2510 by the supplier Exxon Chemicals, NOR-SOLENE® A 100 by the supplier Cray Valley, the resins sold under the reference WINGTACK® 86, WINGTACK® EXTRA and WINGTACK® PLUS by the supplier Cray Valley;

(d) polycyclopentadienes such as those having the reference KOBOGUARD® 5400 sold by the supplier KOBO;

(e) diene resins from cyclopentadiene dimers, such as those derived from the polymerization of a first monomer selected from indene and styrene, and a second monomer selected from dimers of cyclopentadiene such as dicyclopentadiene, methyldicyclopentadiene, other dimers of pentadiene, and mixtures thereof. These resins generally present a molecular weight lying in the range 500 g/mol to 800 g/mol, such as for example those sold under the reference ESCOREZ® 5380, ESCOREZ® 5300, ESCOREZ® 5400, ESCOREZ® 5415, ESCOREZ® 5490, ESCOREZ® 5600, ESCOREZ® 5615, ESCOREZ® 5690, by the supplier Exxon Mobil Chem., and the resins SUKOREZ® SU-90, SUKOREZ® SU-100, SUKOREZ® SU-110, SUKOREZ® SU-100S, SUKOREZ® SU-200, SUKOREZ® SU-210, SUKOREZ® SU-490, SUKOREZ® SU-400, by the supplier Kolon;

(f) diene resins from isoprene dimers such as the terpene resins derived from the polymerization of at least one monomer selected from a-pinene, beta-pinene, limonene, styrene, and mixtures thereof. These resins may present a molecular weight lying in the range 300 g/mol to 2000 g/mol. By way of example, such resins are sold under the name PICCOLYTE A115 by the supplier Hercules, ZONAREZ® 7100 or ZONATAC® 105 LITE by the supplier ARIZONA Chem.

Mention may also be made of hydrogenated resins derived mainly from the polymerization of pentadiene such as those sold under the name EASTOTAC® H-100E, EASTOTAC® H-115E, EASTOTAC® C-100L, EASTOTAC® C-115L, EASTOTAC® H-100L, EASTOTAC® H-115L, EASTOTAC® C-100R, EASTOTAC® C-115R, EASTOTAC® H-100R, EASTOTAC® H-115R, EASTOTAC® C-100W, EASTOTAC® C-115W, EASTOTAC® H-100W, EASTOTAC® H-115W, by the supplier Eastman Chemical Co.

The silicone film forming polymer may be chosen from silicone resins which are cross-linked polyorganosiloxane polymers. The nomenclature of silicone resins is known under the name "MDTQ", the resin being described as a function of the various monomeric siloxane units it includes, each of the letters "MDTQ" characterizing one type of unit.

Examples of commercially available polymethylsilsesquioxane resins that may be mentioned are those that are sold by the supplier Wacker under the reference Resin MK such as Belsil® PMS MK, and by the supplier SHIN-ETSU under the references KR-220L.

Examples of commercially available polypropylsilsesquioxane resins that may be mentioned are those that are sold under the reference DC®670 by the supplier Dow Corning.

Siloxysilicate resins that may be mentioned are trimethylsiloxysilicate resins (TMS) such as those sold under the reference SR1000® by the supplier Momentive Performance Materials or under the reference TMS® 803 by the supplier Wacker. It is also possible to mention trimethylsiloxysilicate resins sold in a solvent such as cyclomethicone, sold under the name "KF-7312J" by the supplier Shin-Etsu, or "DC® 749", "DC® 593" by the supplier Dow Corning.

It is also possible to mention silicone resin copolymers such as the pressure-sensitive adhesive copolymers sold in particular by the supplier Dow Corning under the reference BIO-PSA and described in the document U.S. Pat. No. 5,162, 410, or silicone copolymers derived from the reaction of a silicone resin such as those described above and of a diorganosiloxane such as that described in the document WO 2004/073626.

Suitable examples of polyalkylenes are copolymers of $C_2$-$C_{20}$ alkenes such as polybutene, alkylcelluloses with a $C_1$ to $C_8$, linear or branched alkyl radical, saturated or unsaturated, such as ethylcellulose or propylcellulose, copolymers of vinylpyrrolidone (VP) and in particular copolymers of vinylpyrrolidone and $C_2$ to $C_{40}$ alkene, more preferably $C_3$ to $C_{20}$. Examples of VP copolymers that may be used in the invention and that may be mentioned are polyvinylpyrrolidone (PVP), and the copolymer of VP/vinyl acetate, VP/ethyl methacrylate, butylated polyvinylpyrolidone (PVP), VP/ethyl methacrylate/methacrylic acid, VP/eicosene, VP/hexadecene, VP/triacontene, VP/styrene and VP/acrylic acid/lauryl methacrylate.

The film forming agent may also be a vinyl polymer including at least one motif derived from carbosiloxane dendrimer.

Vinyl polymers including motifs derived from carbosiloxane dendrimer are also suitable for use in the invention.

In particular, the vinyl polymer may have a skeleton and at least one lateral chain that comprises a carbosiloxane dendrimer structure. In the context of the present invention, the term "carbosiloxane dendrimer structure" represents a molecular structure having branched groups having high molecular weights, said structure having a high regularity in the radial direction starting from the bond to the skeleton.

Vinyl polymers grafted with at least one motif derived from carbosiloxane dendrimer that are particularly suitable for the present invention are the polymers sold under the names TIB 4-100, TIB 4-101, TIB 4-120, TIB 4-130, TIB 4-200, FA 4002 ID (TIB 4-202), TIB 4-220, and FA 4001 CM (TIB 4-230) by the supplier Dow Corning.

It is also possible to use silicone polyamides of the polyorganosiloxane type.

These silicone polymers may belong to the following two families:

polyorganosiloxanes comprising at least two groups capable of establishing hydrogen interactions, these two groups being located in the polymer chain; and/or polyorganosiloxanes comprising at least two groups capable of establishing hydrogen interactions, these two groups being located on grafts or branches.

The film-forming agent may also be a linear film-forming ethylenic block polymer that preferably comprises at least one first block and at least one second block having different glass transition temperatures (Tg), said first and second blocks being connected together via an intermediate block comprising at least one constituent monomer of the first block and at least one constituent monomer of the second block.

Advantageously, the first and second blocks of block polymer are incompatible with each other.

The film forming agent may also be chosen from polyacrylates such as polyacrylate-21, and polyacrylate-15, and acrylates copolymer.

The film-forming agent may also be chosen from latex film forming polymers such as polyacrylate latex, polyurethrane latex, and their copolymers.

Suitable examples of latex polymers for use in the present invention are ethylhexyl acrylate/hema copolymer (and) acrylates/diethylaminoethyl methacrylate/ethylhexyl acrylate copolymer (Syntran® PC 5775), styrene/acrylates/ammonium methacrylate copolymer (Syntran® 5760, Syntran® 5009, Syntran® PC5620), polyacrylate-21 (and) acrylates/dimethylaminoethyl methacrylate copolymer (Syntran® PC5100, Syntran® PC5776, Eudragit E 100, Jurymer ET-410C), styrene/acrylates/ammonium methacrylate copolymer (Syntran® 5009 CG), acrylates copolymer (Aculyn® 33A Polymer, Avalure® Ace 210/120/315 Acrylic Copolymer, Carbopol Aqua SF-1®Polymer, Daitosol® 500 AD, Coatex® Co 633, Eliclear® 380/700/4U, Eudragit® L 100, Joncryl® 85, Luviflex® Soft), acrylates/ethylhexyl acrylate copolymer (Daitosol® 5000SJ, Daitosol® 4000SJT, MJA PS34-21, SDP-001). The Syntran® polymers are commercially available from the supplier Interpolymer Corp.

Other suitable examples of latex polymers are polyurethane-35, polyurethane-35, and polyurethane-35.

In other embodiments, the latex polymer is an acrylate latex polymer.

The film-forming agent (s) may be present in the composition in an amount ranging from about 0.01% to about 50% by weight, preferably ranging from about 0.1% to about 30% by weight, or from about 1% to about 25% by weight, or ranging from about 5% to about 20% by weight, relative to the total weight of the composition.

The gelling agent other than the at least one hydrophilic gelling agent is preferably chosen from polysaccharides and organic or mineral, polymeric or molecular lipophilic gelling agents. Said gelling agent may also sometimes be considered to be a film forming agent.

The gelling agents of the polysaccharide type may be chosen from xanthan gum, xanthan derivatives, carrageenans, gellans, alginates, celluloses such as microcrystalline cellulose and cellulose polymers such as hydroxyethylcellulose, hydroxymethylcellulose, hydroxypropylcellulose, methylcellulose, ethylhydroxyethylcellulose, and carboxymethylcellulose, and mixtures thereof.

The lipophilic gelling agents may be chosen from optionally modified clays, fumed silica optionally subjected to a hydrophobic surface treatment, organogelling agents, for example, amides of carboxylic acids, in particular of tricarboxylic acids, diamides with hydrocarbon-based chains each containing from 1 to 22 carbon atoms, polymeric organic lipophilic gelling agents or thickeners other than the at least one silicone elastomer blend comprising at least one silicone cross-polymer dispersed in at least one oil, for example, polycondensates of the polyamide type resulting from condensation between (α) at least one acid chosen from dicarboxylic acids containing at least 32 carbon atoms, such as fatty acid dimers, and (β) an alkylenediamine and in particular ethylenediamine, in which the polyamide polymer comprises at least one carboxylic acid end group esterified or amidated with at least one saturated and linear monoalcohol or one saturated and linear monoamine containing from 12 to 30 carbon atoms, and in particular ethylenediamine/stearyl dilinoleate copolymers such as the product sold under the name Uniclear 100 VG® by the company Arizona Chemical.

Additives

The composition of the invention may further include any additive that is usually used in cosmetics.

Naturally, the person skilled in the art takes care to select any complementary cosmetic additives and/or their quantities in such a manner that the advantageous properties of the composition of the invention is spoilt little, if at all, by the envisaged addition.

Examples of particular additives that may be mentioned are antioxidants, fillers, preservatives, fragrances, neutralizers, fatty acids, thickeners, vitamins, coalescers, plasticizers, and mixtures thereof.

The fillers may be present in the composition at a content lying in the range 0.01% to 50% by weight relative to the total weight of the composition, preferably lying in the range 0.1% to 30% by weight, e.g. lying in the range 1% to 25% by weight, e.g. lying in the range 5% to 20% by weight.

The term "fillers" means particles of any shape, colorless or white, inorganic or synthetic, and insoluble in the composition medium regardless of the temperature at which the composition is manufactured, to the exclusion of fibers. These fillers serve in particular to modify the rheology or the texture of the composition.

The fillers may be organic or inorganic and of any shape, flakes, spherical, or oblong, whatever the crystal shape (e.g. sheets, cubic, hexagonal, orthorombic, etc).

Mention may be made of mica, kaolin, poly-beta-alanine and polyethylene powders, tetrafluoroethylene polymer powders (Teflon®), lauroyl-lysine, starch, boron nitride, hollow polymeric microspheres such as those formed from polyvinylidene chloride/acrylonitrile, such as Expancel® (Nobel Industrie), acrylic acid copolymers (Polytrap® from the supplier Dow Corning) and silicone resin microbeads (e.g. Tospearls® from the supplier Toshiba), particles of polyorganosiloxane elastomers, precipitated calcium carbonate, magnesium carbonate and bicarbonate, hydroxyapatite, hollow silica microspheres (Silica Beads® from the supplier Maprecos), glass or ceramic microcapsules, metallic salts derived from organic carboxylic acids containing 8 to 22 carbon atoms, preferably 12 to 18 carbon atoms, for example zinc, magnesium, or lithium stearate, zinc laurate, and magnesium myristate.

In particular, they may preferably be selected from talc, silica, rice starch, polyamide powders (Nylon®), and polymethylmethacrylate powders, in particular those sold under the name COVABEAD® LH85 by the supplier LCW.

The neutralizers may be selected from amino acids and amine- or amino-based compounds such as amino acids, alkylamines, alkyleneamines, polyamines, and alkoxylated amines.

The neutralizers may be selected from amino acids and amine- or amino-based compounds such as amino acids, alkylamines, polyamines, and alkoxylated amines. A preferred neutralizer for use in the invention is an amino acid suc as arginine. As described earlier, Arginine may also function as an emulsifier when combined with a fatty acid.

In one embodiment of the present invention is a composition which contains so little TEA-stearate that the presence of TEA-stearate does not affect the cosmetic properties of the composition. Preferably, the compositions are substantially free of TEA-stearate (i.e., contain less than about 0.5 percent TEA-stearate), essentially free of TEA-stearate (i.e., contain less than about 0.25 percent TEA-stearate) or free of TEA-stearate (i.e., contain no TEA-stearate).

The compositions of the present invention are in the form of emulsions such as oil in water emulsions and water in oil emulsions, preferably, the compositions of the present invention are oil in water emulsions. Such emulsions will generally be comprised of the liquid fatty phase (also known as an oil phase) and the aqueous phase as described earlier.

According to other preferred embodiments, methods of treating, coating and/or enhancing the appearance of keratinous fibers, such as the eyelashes and/or eyebrows, by applying compositions of the present invention to keratinous fibers in an amount sufficient to treat, care for and/or enhance the appearance of the keratinous fibers are provided. In accordance with these preceding preferred embodiments, the compositions of the present invention are applied topically to the desired area in an amount sufficient to treat, care for and/or enhance the appearance of the keratinous fibers. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

According to a preferred embodiment of the present invention, compositions having improved cosmetic properties such as, for example, improved feel upon application (for example, texture, reduced drag or tackiness, softness, suppleness), increased volume properties and/or increased wear properties, and ease of removal are provided.

According to another preferred embodiment of the present invention, compositions having improved stability such that there is zero or very minimal visual breakage of portions of the compositions from the bulk of the compositions are provided.

According to certain embodiments of the present invention, methods of improving the volumizing and/or thickening properties of a composition, comprising adding at least one semicrystalline polymer, at least one silicone elastomer blend, at least one hydrophilic gelling agent and an aqueous phase to the composition are provided.

According to other embodiments, methods of applying the compositions of the present invention onto keratinous fibers such as eyebrows and/or eyelashes are provided. Compared with compositions (comparative) which do not contain the combination of the at least one semicrystalline polymer, the at least one silicone elastomer blend, and the at least one hydrophilic gelling agent, the compositions of the present invention (inventive) form a smooth and homogeneous film and are easier to apply onto the keratinous fibers.

The composition according to the present disclosure may be manufactured by the known processes generally used in cosmetics.

When the composition of the present invention is a mascara, the composition may be packaged in an applicator product comprising a reservoir and a removable cap for closing the reservoir, for example in a leaktight manner.

The applicator assembly may also comprise a member for applying the composition to keratinous fibers, such as the eyelashes, wherein the applicator member allows the composition to be taken up and also allows the composition taken up to be deposited on the eyelashes. This applicator member can be, for example, securely fastened to the cap for leaktight closure of the assembly.

The applicator assembly may also comprise a draining member (or drainer) for the applicator member, the draining member possibly being securely fastened to the reservoir.

The applicator member may for example, be a mascara brush that is well known to those skilled in the art. Such a brush for instance, comprises bristles arranged radially around a twisted core, such as a metal core. The brush may be of varied shape and may comprise cutout sections. Mascara brushes are described, for example, French Patent No. FR-A-2 607 373, and European Patent Nos. EP-A-611 170, EP-A-811 336, EP-A-811 337 and EP-A-842 620.

Alternatively, the applicator may comprise a comb comprising a plurality of teeth obtained by molding with a support made of thermoplastic material. The applicator may also comprise a comb combined with a brush.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

The following Examples are intended to be non-restrictive and explanatory only, with the scope of the invention being defined by the claims.

The compositions below were prepared by mixing, independently, the components set forth in the following Tables.

Example 1

Inventive Formulas A and B, Mascara Compositions

TABLE 1

| Formula A | | |
|---|---|---|
| Phase | INCI US Name | Weight % |
| A | WATER | 35.47 |
| A | PVP | 1 |
| A | PHENOXYETHANOL | 0.6 |
| A | HYDROLYZED CORN STARCH | 2 |
| A | SODIUM DEHYDROACETATE | 0.2 |
| A | DISODIUM EDTA | 0.1 |
| A | CAPRYLYL GLYCOL | 0.4 |
| A | ARGININE | 1.1 |
| A3 | BUTYLENE GLYCOL | 2 |
| A3 | AMMONIUM POLYACRYLOYLDIMETHYL TAURATE, Hostacerin AMPS ® from Clariant | 1 |
| A4 | IRON OXIDES | 7 |
| B | BEESWAX | 4.85 |
| B | ETHYLENEDIAMINE/STEARYL DIMER DILINOLEATE COPOLYMER, Uniclear 100 VG from Arizona Chemicals | 0.75 |
| B | C30-45 ALKYLDIMETHYLSILYL POLYPROPYLSILSESQUIOXANE (and) PARAFFIN, Dow | 4.55 |

TABLE 1-continued

Formula A

| Phase | INCI US Name | Weight % |
|---|---|---|
|   | Corning SW-8005 C30 Resin Wax from Dow Corning |   |
| B | PARAFFIN, Sasol Wax 5603 from Sasol | 8.5 |
| B | STEARIC ACID | 3.63 |
| B | ADIPIC ACID/DIETHYLENE GLYCOL/GLYCERIN CROSSPOLYMER, Lexorez 100 from Inolex Chemical Company | 0.95 |
| B | VP/EICOSENE COPOLYMER | 1.95 |
| B | STEARETH-20 | 2.95 |
| B | DIMETHICONE (and) DIMETHICONE/VINYL DIMETHICONE CROSSPOLYMER (1.2 active), KSG-16 from Shin Etsu; | 5 |
| B | POLY C10-30 ALKYL ACRYLATE, Intelimer® IPA 13-1 NG from Air Products and Chemicals | 2.5 |
| C | PEG/PPG-17/18 DIMETHICONE, XIAMETER OFX-5220 FLUID from Dow Corning | 0.5 |
| D | ACRYLATES/ETHYLHEXYL ACRYLATE/HEMA COPOLYMER (and) ACRYLATES/DIETHYLAMINOETHYL METHACRYLATE/ETHYLHEXYL ACRYLATE COPOLYMER (and) ISODECETH-6 (and) CAPRYLYL GLYCOL (and) SODIUM LAURETH SULFATE, Syntran® PC 5775, from Interpolymer | 10 |
| E | ALCOHOL DENAT. | 3 |

TABLE 2

Formula B

| Phase | INCI US Name | Weight % |
|---|---|---|
| A | WATER | 35.97 |
| A | PVP | 1 |
| A | PHENOXYETHANOL | 0.6 |
| A | HYDROLYZED CORN STARCH | 2 |
| A | SODIUM DEHYDROACETATE | 0.2 |
| A | DISODIUM EDTA | 0.1 |
| A | CAPRYLYL GLYCOL | 0.4 |
| A | ARGININE | 1.1 |
| A3 | BUTYLENE GLYCOL | 2 |
| A3 | AMMONIUM POLYACRYLOYLDIMETHYL TAURATE, Hostacerin AMPS® from Clariant | 0.5 |
| A4 | IRON OXIDES | 7 |
| B | BEESWAX | 4.85 |
| B | ETHYLENEDIAMINE/STEARYL DIMER DILINOLEATE COPOLYMER, Uniclear 100 VG from Arizona Chemicals | 0.75 |
| B | C30-45 ALKYLDIMETHYLSILYL POLYPROPYLSILSESQUIOXANE (and) PARAFFIN, Dow Corning SW-8005 C30 Resin Wax from Dow Corning | 4.55 |
| B | PARAFFIN, Sasol Wax 5603 from Sasol | 8.5 |
| B | STEARIC ACID | 3.63 |
| B | ADIPIC ACID/DIETHYLENE GLYCOL/GLYCERIN CROSSPOLYMER, Lexorez 100 from Inolex Chemical Company | 0.95 |
| B | VP/EICOSENE COPOLYMER | 1.95 |
| B | STEARETH-20 | 2.95 |
| B | DIMETHICONE (and) DIMETHICONE/VINYL DIMETHICONE CROSSPOLYMER, KSG-16 from Shin Etsu | 5 |
| B | POLY C10-30 ALKYL ACRYLATE, Intelimer® IPA 13-1 NG from Air Products and Chemicals | 2.5 |
| C | PEG/PPG-17/18 DIMETHICONE, XIAMETER OFX-5220 FLUID from Dow Corning | 0.5 |
| D | ACRYLATES/ETHYLHEXYL ACRYLATE/HEMA COPOLYMER (and) ACRYLATES/DIETHYLAMINOETHYL METHACRYLATE/ETHYLHEXYL ACRYLATE COPOLYMER (and) ISODECETH-6 (and) CAPRYLYL GLYCOL (and) SODIUM LAURETH SULFATE, Syntran® PC 5775, from Interpolymer | 10 |
| E | ALCOHOL DENAT. | 3 |

Formulas A and B contained a silicone elastomer blend (KSG-16), a semicrystalline polymer, poly C10-30 alkyl acrylate, and a hydrophilic gelling agent, ammonium polyacryloyldimethyl taurate, for thickening or modifying the viscosity of the formulas.

Process of making the inventive mascara compositions:

Added water to main vessel, began homogenization (200-300 rpm) with rotor stator blade while beginning to heat batch to 90C. Added ingredients of phase A one at a time and mixed until each was uniformly dispersed.

Added phase A3 to main vessel. Added phase A4 and ground pigments for 60 minutes.

In a separate beaker, added ingredients of phase B and heated until all ingredients were melted and homogeneous (approximately 80-90° C.)

Added phase B to main kettle and homogenized for 20 mins.

Removed hot water bath and stopped homogenizing. Switched to sweep blade.

Immediately added ingredients of phase C (including the silicone elastomer blend) and sweep mixed until uniform.

At ~45° C., added phase D, mixed until uniform and continued to mix until batch reached 30° C. Added phase E and continued mixing until batch reached room temperature. Dropped batch and after 16-24H took specs (viscosity, pH, and specific gravity).

Example 2

Comparative Formulas, Mascara Compositions

Comparative mascara compositions were prepared similarly according to the procedure of making the inventive mascara compositions above.

TABLE 3

| INCI US | Weight % | | | | | |
|---|---|---|---|---|---|---|
|  | C | D | E | F | G | H |
| POLY C10-30 ALKYL ACRYLATE, Intelimer® IPA 13-1 NG from Air Products and Chemicals | — | — | — | 2 | 2 | — |
| DIMETHICONE (and) DIMETHICONE/VINYL | — | — | — | 3 | 3 | — |

TABLE 3-continued

| INCI US | Weight % | | | | | |
|---|---|---|---|---|---|---|
| | C | D | E | F | G | H |
| DIMETHICONE CROSSPOLYMER, KSG-16 from Shin Etsu | | | | | | |
| DIMETHICONE (and) DIMETHICONE/PEG-10/15 CROSSPOLYMER, KSG-210 from Shin Etsu | — | — | 3 | — | — | — |
| Waxes: C30-45 ALKYLDIMETHYLSILYL POLYPROPYLSILSESQUIOXANE (and) PARAFFIN, Dow Corning SW-8005 C30 Resin Wax from Dow Corning and BEESWAX and PARAFFIN, Sasol Wax 5603 from Sasol | 18.6 | 18.6 | 18.6 | 18.6 | 17.6 | — |
| Waxes: COPERNICIA CERIFERA (CARNAUBA) WAX and BEESWAX and PARAFFIN, Sasol Wax 5603 from Sasol | — | — | — | — | — | 21.64 |
| HYDROXYETHYLCELLULOSE | 0.4 | 0.4 | 0.4 | 0.2 | 0.2 | 0.9 |
| ACACIA SENEGAL GUM | 1.5 | 1.5 | 1.5 | 0.6 | 0.6 | 3.39 |
| VP/EICOSENE COPOLYMER | 2 | 2 | 2 | 2 | 1.9 | |
| HYDROLYZED CORN STARCH | 2 | 2 | 2 | 2 | 2 | |
| PVP | 1 | 1 | 1 | 1 | 1 | |
| SODIUM POLYMETHACRYLATE | | | | | | 1 |
| CETYL ALCOHOL | | | | | | 2 |
| HYDROGENATED JOJOBA OIL and HYDROGENATED PALM OIL | | | | | | 0.4 |
| ADIPIC ACID/DIETHYLENE GLYCOL/GLYCERIN CROSSPOLYMER, Lexorez 100 from Inolex Chemical Company | 1 | 1 | 1 | 1 | 0.95 | — |
| ETHYLENEDIAMINE/STEARYL DIMER DILINOLEATE COPOLYMER, Uniclear 100 VG from Arizona Chemicals | 0.8 | 0.8 | 0.8 | 0.8 | 0.75 | — |
| STYRENE/ACRYLATES/AMMONIUM METHACRYLATE COPOLYMER (and) SODIUM LAURETH SULFATE (and) CAPRYLYL GLYCOL, Syntran ® 5760 CG from Interpolymer | — | 9 | — | — | — | — |
| ACRYLATES/ETHYLHEXYL ACRYLATE/HEMA COPOLYMER (and) ACRYLATES/DIETHYLAMINOETHYL METHACRYLATE/ETHYLHEXYL ACRYLATE COPOLYMER (and) ISODECETH-6 (and) CAPRYLYL GLYCOL (and) SODIUM LAURETH SULFATE, Syntran ® PC 5775, from Interpolymer | 9 | — | 9 | 9 | 9 | 10 |
| SODIUM DEHYDROACETATE | 0.2 | 0.2 | 0.2 | 0.2 | 0.2 | — |
| PHENOXYETHANOL | 0.6 | 0.6 | 0.6 | 0.6 | 0.6 | 0.5 |
| PEG/PPG-17/18 DIMETHICONE, XIAMETER OFX-5220 FLUID from Dow Corning | 0.5 | 0.5 | 0.5 | 0.5 | 0.5 | 0.5 |
| DISODIUM EDTA | 0.1 | 0.1 | 0.1 | 0.1 | 0.1 | 0.1 |
| ARGININE | 1.1 | 1.1 | 1.1 | 1.1 | 1.1 | — |
| IRON OXIDES | 7 | 7 | 7 | 7 | 7 | 7.14 |
| GLYCOLS | 4 | 4 | 4 | 2.4 | 2.4 | — |
| ALCOHOL DENAT. | 3 | 3 | 3 | 3 | 3 | — |
| PHENYL ETHYL ALCOHOL | — | — | — | — | — | 0.5 |
| STEARIC ACID | 3.63 | 3.63 | 3.63 | 3.63 | 3.63 | — |
| STEARETH-20 | 5 | 5 | — | 3 | 3 | 0.5 |
| WATER | QS 100 | QS 100 | QS 100 | QS 100 | QS 100 | QS 100 |

None of the comparative formulas in Table 3 above employed a hydrophilic gelling agent such as ammonium polyacryloyldimethyl taurate, for thickening or modifying the viscosity of the formulas; instead, the comparative formulas employed acacia senegal gum and hydroxyethylcellulose as thickening or gelling agents. Moreover, Formulas C and D did not contain a silicone elastomer blend nor a semicrystalline polymer, poly C10-30 alkyl acrylate, while Formula E did not contain a semicrystalline polymer. Formulas F and G contained a silicone elastomer blend and a semicrystalline polymer. Formula H did not contain either silicone elastomer blend or semicrystalline polymer.

Example 3

Comparative Testing

Composition Texture and Stability

The texture of the inventive formulas A and B was compared to that of the comparative formulas in Table 3.

Compared to the comparative formulas, the inventive formulas A and B had a smoother and creamier texture and feel and had reduced tackiness and stickiness as evidenced by the good lash separation and soft feel of the lashes. The inventive compositions were also found to be stable after testing them in a controlled chamber such as an oven, after 12 weeks at 45° C. The word "stable" means that there was no phase separation and/or crystallization of the waxes. It also means that there was not visual syneresis or breakage of a portion of the compositions from the bulk.

Cosmetic Benefits

The cosmetic performances of the inventive formulas A and B were compared to those of the comparative formulas in Table 3.

The formulas were applied onto the eyelashes of consumers either by themselves or by a cosmetologist using an applicator.

Compared to the comparative formulas, the inventive formulas A and B demonstrated improved volumizing effects and better product deposit without causing any visible or undesirable clumping or caking on the eyelashes.

At the same time, the inventive formulas were easier to apply and deposited smooth, flat layers of the compositions onto the eyelashes. The lashes were also soft and supple to the touch.

In addition, the formulas were tested for removability with water from coated false eyelashes. It was found that the inventive formulas were easier to remove compared to the comparative formulas.

The volumizing effects of the inventive compositions are demonstrated in Example 4 below.

Example 4

Comparative Testing on Volumizing Effects

The inventive formula B was compared against formula H in terms of breadth differences of the lash fibers (mm) after coating/treating the fibers with the test formulas (2 dips into the composition/15 strokes on the fibers; N=30 fibers per test formula). The widths were measure by image analysis.

TABLE 4

| Treatment | Width differences (post-treated minus pre-treated) | % Volume increase |
|---|---|---|
| Formula B | 0.230 ± 0.068 | 1028 |
| Formula H | 0.195 ± 0.085 | 881 |
| p-value | 0.026 | |

A p-value of less than 0.05 means that the width difference between the two sets of measurements was statistically significant. This shows that the volumizing effect imparted by the inventive composition onto fibers is statistically significantly better compared to that of the comparative formula which did not contain the silicone elastomer blend, the semi-crystalline polymer (poly C10-30 alkyl acrylate) and the hydrophilic gelling agent (ammonium polyacryloyldimethyl taurate).

It is to be understood that the foregoing describes preferred embodiments of the invention and that modifications may be made therein without departing from the spirit or scope of the invention as set forth in the claims.

What is claimed is:

1. A cosmetic composition for making up and/or coating keratinous fibers, said composition comprising:
   (a) at least one semicrystalline polymer, wherein the at least one semicrystalline polymer is poly C10-30 alkyl acrylate;
   (b) at least one silicone elastomer blend comprising at least one silicone cross-polymer dispersed in at least one oil;
   (c) at least one hydrophilic gelling agent, wherein the at least one hydrophilic gelling agent is ammonium polyacryloyldimethyl taurate; and
   (d) an aqueous phase.

2. The cosmetic composition of claim 1, wherein the at least one semicrystalline polymer is present in the cosmetic composition in an amount ranging from about 0.1% to about 20% by weight, relative to the total weight of the composition.

3. The cosmetic composition of claim 1, wherein the at least one semicrystalline polymer is present in the cosmetic composition in an amount ranging from about 1% to about 5% by weight, relative to the total weight of the composition.

4. The cosmetic composition of claim 1, wherein the at least one silicone elastomer blend is at least one silicone cross-polymer dispersed in at least one oil chosen from silicone oils and organic oils.

5. The cosmetic composition of claim 1, wherein the at least one silicone elastomer blend is dimethicone/vinyl dimethicone cross-polymer dispersed in dimethicone.

6. The cosmetic composition of claim 1, wherein the at least one silicone elastomer blend is present in the cosmetic composition in an amount ranging from about 0.1% to about 40% by weight, relative to the total weight of the composition.

7. The cosmetic composition of claim 1, wherein the at least one silicone elastomer blend is present in the cosmetic composition in an amount ranging from about 1% to about 10% by weight, relative to the total weight of the composition.

8. The cosmetic composition of claim 1, wherein the at least one hydrophilic gelling agent is present in an amount ranging from about 0.01% to about 5% by weight, relative to the total weight of the composition.

9. The cosmetic composition of claim 1, wherein the at least one hydrophilic gelling agent is present in an amount ranging from about 0.25% to about 2% by weight, relative to the total weight of the composition.

10. The cosmetic composition of claim 1, wherein the aqueous phase comprises water and/or at least one water-soluble solvent.

11. The cosmetic composition of claim 1, wherein the aqueous phase is present in an amount ranging from about 5% to about 95% by weight, relative to the total weight of the composition.

12. The cosmetic composition of claim 1, wherein the composition comprises an emulsifying system.

13. The cosmetic composition of claim 1, wherein the composition comprises a liquid fatty phase.

14. The cosmetic composition of claim 1, further comprising at least one wax chosen from beeswax, lanolin wax, Chinese insect waxes, rice wax, carnauba wax, candelilla wax, ouricury wax, esparto grass wax, cork fibre wax, sugar cane wax, Japan wax, sumach wax, montan wax, microcrystalline waxes, paraffins, ozokerite, polyethylene waxes, waxes obtained by Fisher-Tropsch synthesis, waxy copolymers, silicone waxes, silsesquioxane resin waxes, fluoro waxes, tacky waxes, and microwaxes, and esters thereof, and mixtures thereof.

15. The cosmetic composition of claim 12, wherein the at least one wax is present in the cosmetic composition in an amount ranging from about 5% to about 40% by weight relative to the total weight of the composition.

16. The cosmetic composition of claim 1, further comprising at least one desired agent chosen from a colorant, a fiber, a cosmetically active agent, a film forming agent, and a gelling agent other than the at least one hydrophilic gelling agent.

17. The cosmetic composition of claim 16, wherein the colorant is chosen from pigments, dyes, nacreous pigments, and pearling agents.

18. The cosmetic composition of claim 16, wherein the fiber is chosen from nylon fibers, rayon fibers, silk fibers, cotton fibers; wool fibers, flax fibers, cellulose fibers, polyamide fibers, viscose fibers, acetate fibers, acrylic fibers, polyolefin fibers, silica fibers, carbon fibers, polytetrafluoroethylene fibers, insoluble collagen fibers, polyester fibers, polyvinyl chloride fibers, polyvinylidene chloride fibers, polyvinyl alcohol fibers, polyacrylonitrile fibers, chitosan fibers, polyurethane fibers, polyethylene phthalate fibers, fibers formed from mixtures of polymers, substantially rectilinear rigid fibers, elastomeric fibers, TDI/trimellitic anhydride copolymer, and mixtures thereof.

19. The cosmetic composition of claim 16, wherein the film forming agent is chosen from acrylates/ethylhexyl acrylate/hema copolymer, acrylates/diethylaminoethyl methacrylate/ethylhexyl acrylate copolymer, styrene/acrylates/ammonium methacrylate copolymer, acrylates/dimethylaminoethyl methacrylate copolymer, polyacrylate-21, polyacrylate-15, acrylates copolymer, hydrolyzed corn starch, pvp, polyurethane-35, polyurethane-34, polyurethane-32, and acrylates/ethylhexyl acrylate copolymer.

20. The cosmetic composition of claim 16, wherein the gelling agent other than the at least one hydrophilic gelling agent is chosen from polysaccharides and organic or mineral, polymeric or molecular lipophilic gelling agents.

21. The cosmetic composition of claim 1, wherein the composition is a mascara composition and the keratinous fibers are the eyelashes.

22. A method for making up and/or enhancing the appearance of keratinous fibers comprising applying to the keratinous fibers, the composition of claim 1.

23. A cosmetic composition for making up and/or coating keratinous fibers, said composition comprising:
  (a) from about 1% to about 5% by weight of a semicrystalline polymer comprising poly C10-30 alkyl acrylate; and
  (b) from about 2% to about 6% by weight of at least one silicone elastomer blend comprising at least one silicone cross-polymer dispersed in at least one oil;
  (c) from about 0.25% to about 2% by weight of at least one hydrophilic gelling agent comprising ammonium polyacryloyldimethyl taurate;
  (d) an aqueous phase;
  (e) at least one colorant; and
  (f) optionally, at least one wax present in an amount less than or equal to 20% by weight;
  (g) all weights being relative to the total weight of the composition.

24. An assembly for packaging and applying a product for coating keratinous fibers, comprising:
  (1) a container comprising a cosmetic composition containing:
    (a) at least one semicrystalline polymer, wherein the at least one semicrystalline polymer is poly C10-30 alkyl acrylate;
    (b) at least one silicone elastomer blend comprising at least one silicone cross-polymer dispersed in at least one oil;
    (c) at least one hydrophilic gelling agent, wherein the at least one hydrophilic gelling agent is ammonium polyacryloyldimethyl taurate; and
    (d) an aqueous phase; and
  (2) an applicator for applying the cosmetic composition to the fibers.

* * * * *